(12) United States Patent
Foody

(10) Patent No.: US 11,946,001 B2
(45) Date of Patent: Apr. 2, 2024

(54) PROCESS AND SYSTEM FOR PRODUCING FUEL

(71) Applicant: Iogen Corporation, Ottawa (CA)

(72) Inventor: Patrick J. Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

(21) Appl. No.: 18/351,862

(22) Filed: Jul. 13, 2023

(65) Prior Publication Data

US 2023/0374394 A1 Nov. 23, 2023

Related U.S. Application Data

(63) Continuation of application No. PCT/CA2022/050612, filed on Apr. 21, 2022.
(Continued)

(51) Int. Cl.
*C10G 45/44* (2006.01)
*B01D 53/00* (2006.01)
(Continued)

(52) U.S. Cl.
CPC .......... *C10G 45/44* (2013.01); *B01D 53/002* (2013.01); *B01D 53/1475* (2013.01);
(Continued)

(58) Field of Classification Search
CPC .................. C10G 3/52; C10G 49/007; C10G 2300/4043; C10G 2300/42;
(Continued)

(56) References Cited

U.S. PATENT DOCUMENTS

| 3,105,811 A | 10/1963 | Engel |
| 4,372,856 A | 2/1983 | Morrison |

(Continued)

FOREIGN PATENT DOCUMENTS

| AU | 2020100873 | 7/2020 |
| AU | 2021102128 | 9/2021 |

(Continued)

OTHER PUBLICATIONS

"Biomass with CO2 Capture and Storage (Bio-CCS) The Way Forward for Europe", European Technology Platform for Zero Emission Fossil Fuel Power Plants (2012).
(Continued)

*Primary Examiner* — Brian A McCaig
(74) *Attorney, Agent, or Firm* — Knobbe Martens Olson & Bear LLP

(57) ABSTRACT

A process and/or system for producing fuel using renewable hydrogen having a reduced carbon intensity. The renewable hydrogen is produced in a hydrogen production process comprising methane reforming, wherein at least a portion of the feedstock for the hydrogen production process comprises upgraded biogas sourced from a plurality of biogas plants. Each of the upgraded biogases is produced in a process that includes collecting biogas comprising methane and carbon dioxide, capturing at least 50% of the carbon dioxide originally present in the collected biogas and producing the upgraded biogas. Storage of the captured carbon dioxide reducing a carbon intensity of the fuel, without having to provide carbon capture and storage of carbon dioxide from hydrogen production.

20 Claims, 3 Drawing Sheets

Related U.S. Application Data

(60) Provisional application No. 63/201,301, filed on Apr. 22, 2021.

(51) Int. Cl.
  *B01D 53/14* (2006.01)
  *B01D 53/22* (2006.01)
  *C01B 3/34* (2006.01)
  *C01B 32/50* (2017.01)
  *C02F 11/04* (2006.01)
  *C10G 3/00* (2006.01)
  *C10G 49/00* (2006.01)
  *C02F 103/20* (2006.01)

(52) U.S. Cl.
  CPC ............ *B01D 53/229* (2013.01); *C01B 3/34* (2013.01); *C01B 32/50* (2017.08); *C02F 11/04* (2013.01); *C10G 3/52* (2013.01); *C10G 49/007* (2013.01); *B01D 2252/204* (2013.01); *B01D 2257/504* (2013.01); *C01B 2203/0216* (2013.01); *C01B 2203/0233* (2013.01); *C01B 2203/0244* (2013.01); *C01B 2203/0405* (2013.01); *C01B 2203/0415* (2013.01); *C01B 2203/046* (2013.01); *C01B 2203/0475* (2013.01); *C01B 2203/065* (2013.01); *C01B 2203/1241* (2013.01); *C01B 2203/86* (2013.01); *C02F 2103/20* (2013.01); *C10G 2300/1003* (2013.01); *C10G 2300/1011* (2013.01); *C10G 2300/4043* (2013.01); *C10G 2300/42* (2013.01); *C10G 2400/02* (2013.01); *C10G 2400/04* (2013.01); *C10G 2400/08* (2013.01)

(58) Field of Classification Search
  CPC ............ C10G 2400/02; C10G 2400/04; C10G 2400/08; C01B 3/34; C01B 2203/0216; C01B 2203/065; C01B 2203/86; B01D 53/1475; B01D 2257/504; C02F 11/04; C02F 2103/20
  See application file for complete search history.

(56) References Cited

U.S. PATENT DOCUMENTS

| | | | |
|---|---|---|---|
| 6,503,298 B1 | 1/2003 | Monzyk et al. | |
| 7,014,768 B2 | 3/2006 | Li et al. | |
| 7,332,146 B1 | 2/2008 | Huang et al. | |
| RE40,419 E * | 7/2008 | Norbeck | C10G 2/32 |
| | | | 518/706 |
| 7,691,182 B1 | 4/2010 | Muradov et al. | |
| 7,794,690 B2 | 9/2010 | Abatzoglou et al. | |
| 7,931,888 B2 | 4/2011 | Drnevich et al. | |
| 7,951,296 B2 | 5/2011 | Williams | |
| 7,972,082 B2 | 7/2011 | Augenstein et al. | |
| 8,021,464 B2 | 9/2011 | Gauthier et al. | |
| 8,057,773 B2 | 11/2011 | MacArthur et al. | |
| 8,137,422 B2 | 3/2012 | Licht et al. | |
| 8,268,044 B2 | 9/2012 | Wright et al. | |
| 8,318,130 B2 * | 11/2012 | Grimes | B01J 19/2485 |
| | | | 205/637 |
| 8,460,630 B2 | 6/2013 | Niitsuma et al. | |
| 8,470,567 B2 | 6/2013 | Facey et al. | |
| 8,475,566 B2 | 7/2013 | Find | |
| 8,496,908 B1 | 7/2013 | Genkin et al. | |
| 8,658,026 B2 | 2/2014 | Foody et al. | |
| 8,673,056 B2 | 3/2014 | De Bas et al. | |
| 8,673,135 B2 | 3/2014 | Colyar et al. | |
| 8,679,439 B2 | 3/2014 | Randhava et al. | |
| 8,753,854 B2 | 6/2014 | Foody | |
| 8,852,456 B2 | 10/2014 | Valentin et al. | |
| 8,900,546 B2 | 12/2014 | Van De Graaf et al. | |
| 8,916,735 B2 | 12/2014 | McAlister | |
| 8,945,373 B2 | 2/2015 | Foody | |
| 8,974,669 B2 | 3/2015 | Del Porto | |
| 8,980,211 B2 | 3/2015 | Timmins | |
| 8,987,175 B2 | 3/2015 | Van Den Berg et al. | |
| 9,028,794 B2 | 5/2015 | Darde et al. | |
| 9,038,435 B2 | 5/2015 | Wang | |
| 9,040,271 B2 | 5/2015 | Foody | |
| 9,045,337 B2 | 6/2015 | Kuku | |
| 9,108,894 B1 | 8/2015 | Foody et al. | |
| 9,163,180 B2 | 10/2015 | Marion et al. | |
| 9,163,188 B2 | 10/2015 | Forsyth et al. | |
| 9,381,493 B2 | 7/2016 | Kirk et al. | |
| 9,506,605 B2 | 11/2016 | Paget et al. | |
| 9,701,535 B2 | 7/2017 | Iaquaniello et al. | |
| 9,816,035 B2 | 11/2017 | Lehoux et al. | |
| 9,963,665 B2 | 5/2018 | Feldmann | |
| 10,093,540 B2 | 10/2018 | Foody | |
| 10,106,746 B2 | 10/2018 | Boon et al. | |
| 10,228,131 B2 | 3/2019 | Merritt, Jr. | |
| 10,302,357 B2 | 5/2019 | Hernandez et al. | |
| 10,414,649 B2 | 9/2019 | Denton et al. | |
| 10,421,663 B2 | 9/2019 | Foody | |
| 10,557,338 B2 | 2/2020 | Rhodes et al. | |
| 10,577,248 B2 | 3/2020 | Haper, Jr. | |
| 10,723,621 B2 | 7/2020 | Foody | |
| 10,760,024 B2 | 9/2020 | Foody et al. | |
| 10,927,008 B2 | 2/2021 | Raaheim et al. | |
| 10,981,784 B2 | 4/2021 | Foody | |
| 11,168,339 B1 | 9/2021 | Stepany et al. | |
| 11,204,271 B2 | 12/2021 | Williams et al. | |
| 11,293,035 B2 | 4/2022 | Ludtke et al. | |
| 11,299,686 B2 | 4/2022 | Foody et al. | |
| 11,760,630 B2 | 9/2023 | Foody | |
| 11,807,530 B2 | 11/2023 | Foody | |
| 2003/0111410 A1 | 6/2003 | Branson | |
| 2004/0111968 A1 | 6/2004 | Day et al. | |
| 2006/0207178 A1 | 9/2006 | Hsu | |
| 2007/0295593 A1 | 12/2007 | Martinez | |
| 2008/0159938 A1 | 7/2008 | Mauthner et al. | |
| 2008/0262701 A1 | 10/2008 | Williams et al. | |
| 2008/0280338 A1 | 11/2008 | Hall et al. | |
| 2009/0162914 A1 | 6/2009 | Offerman et al. | |
| 2009/0255181 A1 | 10/2009 | Rhinesmith et al. | |
| 2010/0015680 A1 | 1/2010 | Van Groenestijn et al. | |
| 2010/0047160 A1 | 2/2010 | Allam | |
| 2010/0071429 A1 | 3/2010 | Von Nordenskjold | |
| 2010/0076238 A1 | 3/2010 | Brandvold et al. | |
| 2010/0158792 A1 | 6/2010 | Drnevich et al. | |
| 2010/0205863 A1 | 8/2010 | Biollaz et al. | |
| 2010/0228067 A1 | 9/2010 | Peterson et al. | |
| 2010/0297749 A1 | 11/2010 | Aravanis et al. | |
| 2011/0158858 A1 | 6/2011 | Alves Ramalho Gomes | |
| 2011/0175032 A1 | 7/2011 | Gunther | |
| 2011/0226997 A1 | 9/2011 | Goruney et al. | |
| 2011/0229404 A1 | 9/2011 | Guo et al. | |
| 2011/0305627 A1 | 12/2011 | Gupta et al. | |
| 2012/0058045 A1 | 3/2012 | Beckman et al. | |
| 2012/0165581 A1 | 6/2012 | Dupassieux et al. | |
| 2012/0270119 A1 | 10/2012 | Raaheim et al. | |
| 2012/0291351 A1 | 11/2012 | Bool et al. | |
| 2013/0023707 A1 | 1/2013 | Keefer et al. | |
| 2013/0097929 A1 | 4/2013 | Pham et al. | |
| 2013/0161235 A1 | 6/2013 | Foody | |
| 2013/0164806 A1 | 6/2013 | Foody | |
| 2013/0345325 A1 | 12/2013 | Lecomte et al. | |
| 2014/0023671 A1 | 1/2014 | Paul et al. | |
| 2014/0186258 A1 | 7/2014 | Allidieres | |
| 2014/0360485 A1 | 12/2014 | Saxena | |
| 2015/0038599 A1 * | 2/2015 | Kresnyak | C01B 3/34 |
| | | | 518/702 |
| 2015/0133701 A1 * | 5/2015 | Townsend | C01B 3/48 |
| | | | 568/885 |
| 2015/0225233 A1 | 8/2015 | Foody | |
| 2015/0376801 A1 | 12/2015 | Bairamijamal | |
| 2016/0060537 A1 | 3/2016 | Hsu | |
| 2016/0264418 A1 | 9/2016 | Leclerc et al. | |
| 2017/0001142 A1 | 1/2017 | Rayner et al. | |
| 2017/0022424 A1 | 1/2017 | Chapus et al. | |

(56) References Cited

U.S. PATENT DOCUMENTS

| | | |
|---|---|---|
| 2017/0051318 A1 | 2/2017 | Hakalehto |
| 2017/0073227 A1* | 3/2017 | Dybkjær .................. C10G 2/30 |
| 2017/0130582 A1 | 5/2017 | Hsu |
| 2017/0152453 A1 | 6/2017 | Goerz |
| 2017/0158503 A1 | 6/2017 | Foody et al. |
| 2018/0079672 A1 | 3/2018 | Meyer |
| 2018/0251694 A1 | 9/2018 | Foody et al. |
| 2018/0291278 A1 | 10/2018 | Jack et al. |
| 2019/0352177 A1 | 11/2019 | Denton et al. |
| 2019/0359894 A1 | 11/2019 | Heidel et al. |
| 2020/0078728 A1 | 3/2020 | Iaquaniello et al. |
| 2020/0087576 A1 | 3/2020 | Marker et al. |
| 2020/0096254 A1 | 3/2020 | Cardon et al. |
| 2020/0148964 A1 | 5/2020 | Foody et al. |
| 2020/0222874 A1 | 7/2020 | Manenti |
| 2020/0283920 A1 | 9/2020 | Bairamijamal |
| 2020/0307997 A1 | 10/2020 | Tranier |
| 2021/0078888 A1 | 3/2021 | Kanu |
| 2021/0140054 A1 | 5/2021 | Park et al. |
| 2021/0155864 A1 | 5/2021 | Foody et al. |
| 2021/0221679 A1 | 7/2021 | Foody |
| 2021/0275961 A1 | 9/2021 | Foody et al. |
| 2021/0285017 A1 | 9/2021 | Feldmann et al. |
| 2021/0317377 A1 | 10/2021 | Foody et al. |
| 2021/0324282 A1 | 10/2021 | Foody et al. |
| 2022/0042406 A1 | 2/2022 | Whikehart et al. |
| 2022/0119269 A1 | 4/2022 | Huckman et al. |
| 2022/0127211 A1 | 4/2022 | Whitmore |
| 2022/0134298 A1 | 5/2022 | Marker et al. |
| 2022/0177792 A1 | 6/2022 | Foody et al. |
| 2022/0213511 A1 | 7/2022 | Mann et al. |
| 2023/0295523 A1 | 9/2023 | Foody |

FOREIGN PATENT DOCUMENTS

| | | |
|---|---|---|
| CA | 2739420 | 9/2011 |
| CA | 3039567 | 4/2018 |
| CN | 110776941 | 2/2020 |
| CN | 113353886 | 9/2021 |
| DE | 10 2013 011 289 | 1/2015 |
| EP | 2 386 621 | 11/2011 |
| EP | 2 616 530 | 4/2012 |
| EP | 2 724 081 | 12/2012 |
| EP | 2 944 606 | 11/2015 |
| EP | 3 085 766 | 10/2016 |
| EP | 2 547 619 | 10/2017 |
| EP | 3 484 811 | 1/2018 |
| EP | 4 043 089 | 8/2022 |
| ES | 2490066 | 9/2014 |
| FR | 2978961 | 2/2013 |
| GB | 2 466 554 | 6/2010 |
| GB | 2 585 987 | 11/2021 |
| GB | 2 589 198 | 11/2021 |
| GB | 2 596 675 | 1/2022 |
| GB | 2 592 531 | 4/2022 |
| RU | 2 711 634 | 1/2020 |
| WO | WO 2003/051803 | 6/2003 |
| WO | WO 2008/044929 | 4/2008 |
| WO | WO 2008/109122 | 9/2008 |
| WO | WO 2009/126379 | 10/2009 |
| WO | WO 2010/047815 | 4/2010 |
| WO | WO 2010/051622 | 5/2010 |
| WO | WO 2010/080407 | 7/2010 |
| WO | WO 2010/124030 | 10/2010 |
| WO | WO 2011/092136 | 8/2011 |
| WO | WO 2011/101137 | 8/2011 |
| WO | WO 2012/093041 | 7/2012 |
| WO | WO 2013/029171 | 3/2013 |
| WO | WO 2013/131916 | 9/2013 |
| WO | WO 2014/014803 | 1/2014 |
| WO | WO 2015/010201 | 1/2015 |
| WO | WO-2015042315 A1 * | 3/2015 ............ B01D 53/04 |
| WO | WO 2016/101076 | 6/2016 |
| WO | WO 2018/187716 | 10/2018 |
| WO | WO 2019/129858 | 7/2019 |
| WO | WO 2019/185315 | 10/2019 |
| WO | WO 2020/010430 | 1/2020 |
| WO | WO 2021/003564 | 1/2021 |
| WO | WO 2021/035352 | 3/2021 |
| WO | WO 2021/035353 | 3/2021 |
| WO | WO 2021/062397 | 4/2021 |
| WO | WO 2021/110757 | 6/2021 |
| WO | WO 2021/142528 | 7/2021 |
| WO | WO 2021/175662 | 9/2021 |
| WO | WO 2021/180805 | 9/2021 |
| WO | WO 2021/189137 | 9/2021 |
| WO | WO 2021/203176 | 10/2021 |
| WO | WO 2021/217269 | 11/2021 |
| WO | WO 2022/193007 | 9/2022 |
| WO | WO 2022/217365 | 10/2022 |
| WO | WO 2022/221954 | 10/2022 |
| WO | WO 2022/229838 | 11/2022 |
| WO | WO 2022/246546 | 12/2022 |
| WO | WO 2022/253460 | 12/2022 |
| WO | WO 2023/283721 | 1/2023 |
| WO | WO 2023/049993 | 4/2023 |
| WO | WO 2023/049994 | 4/2023 |
| WO | WO 2023/092138 | 5/2023 |
| WO | WO 2023/097403 | 6/2023 |
| WO | WO 2023/097404 | 6/2023 |
| WO | WO 2023/197064 | 10/2023 |
| WO | WO 2023/197065 | 10/2023 |
| WO | WO 2023/197066 | 10/2023 |

OTHER PUBLICATIONS

"Clarification on Compliance with CertifHy Green Hydrogen Criteria for FCH JU Projects", www.fch.europa.eu Access date Jul. 27, 2022.

"Clean and Renewable Energy from Pulp Mill Waste Using Microsludge and Anaerobic Digestion", Paradigm Environmental Technologies Inc., 2011, pp. 1-2.

"Hydrogen in a Low-Carbon Economy", Committee on Climate Change, Nov. 2018.

"Hydrogen Strategy for Canada Seizing the Opportunities for Hydrogen" Access date Jan. 27, 2022.

"Natural Gas Processing: The Crucial Link Between Natural Gas Production and Its Transportation to Market", Energy Information Administration, Office of Oil and Gas, Jan. 2006, pp. 1-11.

"Part II—Environmental Protection Agency—40 CFR Part 80 Regulation of Fuels and Fuel Additives: Changes to Renewable Fuel Standard Program; Final Rule", Federal Register, vol. 75(58), Mar. 26, 2010, in 236 pages. URL: https://www.gpo.gov/fdsys/pkg/FR-2010-03-26/pdf/2010-3851.pdf.

"RTFO Guidance Part One Process Guidance", Department for Transport, version 11.0, Apr. 2018, in 75 pages.

"RTFO Guidance Part One Process Guidance", Department for Transport, version Jan. 2020, used for reporting under the Renewable Transport Fuel Obligations Order 2007 No. 3072, in 71 pages.

"The Role of Biogas & RNG in Hydrogen Production & Decarbonization", Bayo Tech (2020).

"Zero Carbon Hydrogen—Is it Achievable?" https://www.wsp.com/en-GB/insights/zero-carbon-hydrogen-is-it-ievable#:~:text=By%20balancing%20hydrogen%20production%20between,for%20the%20decarbonisation%20of%20heat. Access date: Mar. 5, 2021.

"An Introduction to Petroleum Refining and the Production of Ultra Low Sulfur Gasoline and Diesel Fuel", MathPro, Oct. 2011 (Access Date: Aug. 13, 2020), in 38 pages. URL: https://theicct.org/sites/default/files/publications/ICCT05_Refining_Tutorial_FINAL_R1.pdf.

"Blue Hydrogen—Groundbreaking Solutions for Hydrogen Production at Scale", Topsoe A/S, Denmark, (2022) 11 pages.

Transportation Fuels from Biomass via IH$^2$ Technology, IEA Bioenergy Conference, Nov. 2012, pp. 1-25.

Adair, Blake, "Ammonia: Transitioning to Net-Zero Future", Nutrien (2022).

Al-Qahtani, et al., "Uncovering the True Cost of Hydrogen Production Routes Using Life Cycle Monetisation", Applied Energy 281 (2021) 15958.

(56) References Cited

OTHER PUBLICATIONS

Alves et al., "Overview of Hydrogen Production Technologies from Biogas and the Applications in Fuel Cells", International Journal of Hydrogen Energy (2010) 1-11.
Ambrosetti et al., "A Numerical Investigation of Electrically-Heated Methane Steam Reforming Over Structured Catalysts", Frontiers in Chemical Engineering, 3 (2021) 747636.
Antonini et al, "Biomass to Hydrogen with CCS: can we go negative", https://www.sintef.no/globalassets/project/elegancy/documents/webinar3a/04-elegancy-final-presentation-ca-v2.pdf, Access date: Nov. 7, 2022.
Antonini et al, "Hydrogen Production from Natural Gas and Biomethane with Carbon Capture and Storage—A Techno-Environmental Analysis", Sustainable Energy Fuels, 4 (2020) 2967.
Arora et al. "Small-scale Ammonia Production from Biomass: A Techno-enviro-economic perspective." Industrial & Engineering Chemistry Research 55.22 (2016) 6422-6434.
Baker et al., "Hydrolysis of Cellulose Using Ternary Mixtures of Purified Cellulases," Applied Chemistry and Biotechnology, 1998, vol. 70-72, pp. 395-403.
Boerrigter, "Green gas (SNG) in the Dutch Energy Infrastructure," Energy Research Centre of the Netherlands, ECN-RX-06-072, Mar. 30, 2006, pp. 1-11.
Boland, S., et al., "GHG Emissions Reductions due to the RFS2", Life Cycle Associates, 2015, pp. 1-14.
Borjesson et al., "Biogas as a resource-efficient vehicle fuel", Trends in Biotechnology, 2007, vol. 26, Issue 1, pp. 7-13.
Brau et al., "Hydrogen for Oil Refining via Biomass Indirect Steam Gasification: Energy and Environmental Targets", Clean Techn. Environ. Policy (2013) 15, 501-512.
Brau Jean-Florian., "Production of Hydrogen for Oil Refining by Thermal Gasification of Biomass: Process Design, Integration and Evaluation", Thesis (2013) Chambers University of Technology, Sweden.
British Columbia BCBN Hydrogen Study Final Report https://www2.gov.bc.ca/assets/gov/government/ministries-organizations/zen-bcbn-hydrogen-study-final-v6.pdf, Access Date: Apr. 4, 2021.
Brown, Trevor. "Renewable Hydrogen for Sustainable Ammonia Production." Chemical Engineering Progress 115.8 (2019) 47-53.
California Executive Order S-01-07, Office of the Governor, Signed Jan. 18, 2007, in 2 pages.
Carbolea, Animal Manures, Accessed Nov. 22, 2017, in 6 pages. URL: www.carbolea.ul.ie/manures.php.
Clean Energy Strategies for Local Governments, 7.4 Landfill Methane Utilization, Dec. 10, 2008, pp. 1-34.
Collins, Leigh, "New Clean Hydrogen Production Tax Credit of up to $3/Kg Approved by US House, Paving Way for Cheap Green H2" Access date Jul. 26, 2022.
Cortright et al., "Hydrogen from catalytic reforming of biomass-derived hydrocarbons in liquid water", Nature, Aug. 2002, vol. 418, pp. 964-967.
Cruz et al., "Exergy Analysis of Hydrogen Production via Biogas Dry Reforming", International Journal of Hydrogen Energy, V 43, I 26, (2018) 11688-11695.
Cruz et al., "Petroleum Refinery Hydrogen Production Unit: Exergy [sic] and Production Cost Evaluation", International Journal of Thermodynamics, Dec. 2008, vol. 11, No. 4, pp. 187-193.
Definition of "Crude Oil", Random House Unabridged Dictionary, 2nd Ed., New York, 1993.
Dinca, et al., "CO2 Capture from Syngas Generated by a Biomass Gasification Power Plant with Chemical Absorption Process", Energy (2018).
Energy Independence and Security Act of 2007, United States Cong.
Energy Independence and Security Act of 2007, 110th Cong., Pub. L. 110-140, Enacted Dec. 19, 2007, in 310 pages.
EPA, 2008b. *Clean Energy Strategies for Local Governments*, 7.4: *Landfill Methane Utilization, Draft*. Landfill Methane Outreach Program (LMOP), Climate Change Division, U.S. EPA. Dec. 10, 2008, in 34 pages. URL: https://www.epa.gov/sites/production/files/2015-12/documents/landfills.pdf.

EPA, An Overview of Renewable Natural Gas from Biogas, Jul. 2020.
European Commission, "Renewable energy—Method for Calculating the Share of Renewables in the Case of Co-processing", Feedback from: Iogen Corporation, Feedback reference F3325697 submitted on Jul. 20, 2022. URL: https://ec.europa.eu/info/law/better-regulation/have-your-say/initiatives/12711-Renewable-energy-method-for- calculating-the-share-of-renewables-in-the-case-of-co-processing/F3325697_en Access Date: Oct. 26, 2022.
Ewing et al., "Hydrogen on the Path to Net Zero—Costs and Climate Benefits", Pembina institute, Jul. 2020.
Ferreira-Aparicio et al., "New Trends in Reforming Technologies: from Hydrogen Industrial Plants to Multifuel Microreformers", Catalysis Reviews, 2005, vol. 47, pp. 491-588.
Final Assessment Report "Landfill Biogas Recovery and Utilization at the Santo Andre Municipal Sanitary Landfill Santo Andre, Brazil", Prepared under U.S. Environmental Protection Agency Landfill Methane Outreach Program, Sep. 2008, pp. 1-31.
Full et al., A New Perspective for Climate Change Mitigation—Introducing Carbon-Negative Hydrogen Production from Biomass with Carbon Capture and Storage (HYBECCS), Sustainability (2021) 13 4026.
Gencer, Emre, et al. "Sustainable Production of Ammonia Fertilizers from Biomass." Biofuels, Bioproducts and Biorefining 14.4 (2020) 725-733.
Ghavam et al. "Sustainable Ammonia Production Processes." Frontiers in Energy Research 9 (2021) 34.
Gruia, Practical Advances in Petroleum Processing, vol. 1, Ed. by Chang S. Hsu and Paul R. Robinson, Springer, New York, Chapter 8, "Recent Advances in Hydrocracking", 2006, pp. 219-255.
Guidance for the Certification of Co-Processing, ISCC System GmbH, 2017, Version 1.1, Access date: Aug. 7, 2020, in 8 pages. URL: https://www.iscc-system.org/wp-content/uploads/2017/02/ISCC-Guidance-Document-203-01_Co-processing-requirements.pdf.
Hakawati et al., "What is the most energy efficient route for biogas utilization: Heat, electricity or transport?", Applied Energy, Nov. 2017, vol. 206, pp. 1076-1087.
Hanson, P., "Increasing Renewable Content with the Mass Balance Approach", NNFCC, Mar. 2019 (Access date: Jan. 18, 2022), in 3 pages. URL: https://www.nnfcc.co.uk/files/mydocs/Mass%20Balance.pdf.
Hengeveld et al., "When does decentralized production of biogas and centralized upgrading and injection into the natural gas grid make sense?", Biomass and Bioenergy, Jun. 2014, vol. 67, pp. 363-371.
Hidalgo, Maria, "Biomethane and Biohydrogen: the Future of Energy is Here", CARTIF Blog, Energy and Environment, Mar. 22, 2021, Access Date: Feb. 17, 2022.
Hovland, J et al., "Compression of raw biogas—A feasibility study", Tel-Tek, Apr. 2017, Report No. 2217020-1, in 12 pages.
Howorth et al., "How Green is Blue Hydrogen", Energy Sci. Eng. (2021) 9 1676-1687.
IEAGHG Technical Review 2017-TR2, Feb. 2017. Techno-Economic Evaluation of SMR Based Standalone (Merchant) Hydrogen Plant with CCS, in 286 pages. URL: https://ieaghg.org/exco_docs/2017-02.pdf. (This document uploaded in two parts).
IEAGHG Technical Review 2017-TR3, Mar. 2017. Reference data and Supporting Literature Reviews for SMR based Hydrogen Production with CCS, in 131 pages. URL: https://ieaghg.org/publications/technical-reports/reports-list/10-technical-reviews/778-2017-tr3-reference-data-supporting-literature-reviews-for-smr-based-hydrogen-production-with-ccs. (This document uploaded in three parts).
Jechura, J., "Hydroprocessing: Hydrotreating & Hydrocracking—Chapters 7 & 9", Colorado School of Mines, updated Jul. 12, 2018, in 56 pages. URL: https://inside.mines.edu/~jjechura/Refining/08_Hydroprocessing.pdf.
Jesper et al. "Bio-SNG Potential Assessment: Denmark 2020," Riso National Laboratory for Sustainable Energy, Riso-R-1754, Nov. 2010, pp. 1-85.

(56) References Cited

OTHER PUBLICATIONS

Krich et al., Biomethane from Dairy Waste, "A Sourcebook for the Production and Use of Renewable Natural Gas in California", Jul. 2005, pp. 66-67 and pp. 81-106.

Kurokawa et al., "Energy-Efficient Distributed Carbon Capture in Hydrogen Production from Natural Gas", Energy Procedia 4 (2011) 674-680.

Latvala "Using Biogas in the Production of Liquid Transport Fuels as Hydrogen Source", Second Nordic Biogas Conference, Malmo, Sweden, 2008, pp. 1-13.

Marcoberardino et al., "Green Hydrogen Production from Raw Biogas: A Techno-Economic Investigation of Conventional Processes Using Pressure Swing Adsorption Unit", Processes 6 (2018) 19.

Mcphail et al., The Renewable Identification System and U.S. Biofuel Mandates, USDA, BIO-03, Nov. 2011, in 24 pages.

Mezei, "Options for Upgrading Digester Biogas to Pipeline Quality", Flotech Services, Apr. 2010, pp. 1-15.

Milbrandt et al., "Biogas and Hydrogen Systems Market Assessment", National Renewable Energy Laboratory (NREL). Technical Report NREL/TP-6A20-63596, Mar. 2016.

Milne et al., "Hydrogen from Biomass State of the Art and Research Challenges", National Renewable Energy Laboratory, A Report for the International Energy Agency Agreement on the Production and Utilization of Hydrogen Task 16, Hydrogen from Carbon-Containing Materials, 2002, pp. 1-78.

Mozaffarian et al. "Green Gas (SNG) Production by Supercritical Gasification of Biomass," Energy Research Centre of the Netherlands, ENC-C-04-081, Nov. 2004, pp. 1-71.

Muradov et al., "Hydrogen production by catalytic processing of renewable methane-rich gases", Int. J. of Hydrogen Energy, 2008, vol. 33, pp. 2023-2035.

Najafpour et al., "Hydrogen as clean fuel via continuous fermentation by anaerobic photosynthetic bacteria, Rhodospirillum rubrum", African Journal of Biotechnology, Oct. 2004, vol. 3, Issue 10, pp. 503-507.

Naqvi, Syed, "Hydrogen Production", PEP Report 32C, SRI Consulting (2007).

Ni, et al., "An Overview of Hydrogen Production from Biomass", Fuel Processing Technology 87 (2006) 461-472.

Oni et al., "Comparative Assessment of Blue Hydrogen from Steam Methane Reforming, Autothermal Reforming, and Natural Gas Decomposition Technologies for natural gas-producing regions", Energy Conversion and Management 254 (2022) 115245.

Parkinson et al., "Hydrogen Production using Methane: Techno-Economics of Decarbonizing Fuels and Chemicals", International Journal of Hydrogen Energy, 43 (2018) 2540.

Prospects for Hydrogen from Biomass, IEA Hydrogen Implementing Agreement, Annex 16, Subtask B, Final Report, Jun. 2006, pp. 1-69.

Rapier, Robert "Estimating the Carbon Footprint of Hydrogen Production", Forbes, Jun. 6, 2020.

Rau et al., "Production of Hydrogen by Autothermal Reforming of Biogas", Energy Procedia 120 (2017) 294-301.

Regalbuto, "An NSF Perspective on Next Generation Hydrocarbon Biorefineries", Computers and Chemical Engineering, 2010, vol. 34, pp. 1393-1396.

Robinson et al., Practical Advances in Petroleum Processing, vol. 1, Ed. by Chang S. Hsu and Paul R. Robinson, Springer, New York, Chapter 7, "Hydrotreating and Hydrocracking: Fundamentals", 2006, pp. 177-218.

Rosa et al., "Potential for hydrogen production from sustainable biomass with carbon capture and storage", Renewable and Sustainable Energy Reviews, Apr. 2022, vol. 157, 112123.

Salary, et al., "Design of Oil Refineries Hydrogen Network Using Process Integration Principles", Iran. J. Chem. Chem. Eng., 2008, vol. 27, No. 4, pp. 49-64.

Sanchez et al., "Biomass Based Sustainable Ammonia Production", 2019 AIChE Annual Meeting. AIChE, 2019.

Santos, Stanley, "Understanding the Potential of CCS in Hydrogen Production", Process Industry CCS Workshop (2015).

Schanbacher, "Anaerobic Digestion: Overview and Opportunities", Waste to Energy Workshop: Advances and Opportunities for Ohio's Livestock and Food Processing Industries, OARDC, Apr. 7, 2009, pp. 1-28.

Schill, Susanne, "Iowa to Get First Biomass-to-Ammonia Plant", https://biomassmagazine.com/articles/2613/iowa-to-get-first-biomass-to-ammonia-lant/#:~:text=SynGest%20Inc.%20has%20secured%20a,deploy%20in%20its%20first%20plant., Access date: Feb. 17, 2022.

Schimmel et al., "Determining the renewability of co-processed fuels; Final Report", ECOFYS, Apr. 2018, in 34 pages.

Serrano-Ruiz et al., "Catalytic Routes for the Conversion of Biomass into Liquid Hydrocarbon Transportation Fuels", Energy & Environmental Science, 2011, vol. 4, pp. 83-89.

Shiga et al., "Large-Scale Hydrogen Production from Biogas", International Journal of Hydrogen Energy, 1998, vol. 23, No. 8, pp. 631-640.

Show et al., "Design of Bioreactors for Biohydrogen production", Journal of Scientific & Industrial Research, vol. 67 (2008), pp. 941-949.

Spath et al., "Life Cycle Assessment of Hydrogen Production via Natural Gas Steam Reforming", National Renewable Energy Laboratory, NREL/TP-570-27637, Feb. 2001, in 33 pages.

Stavrakas et al., "Striving Towards the Deployment of Bio-energy with Carbon Capture and Storage (BECCS): A review of Research Priorities and Assessment Needs", Sustainability 2018, 10, 2206.

Streb et al., "Novel Adsorption Process for Co-Production of Hydrogen and CO2 from a Multicomponent Stream—Part 2: Application to Steam Methane Reforming and Autothermal Reforming Gases", Ind. Eng. Chem. Res. 59 (2020) 10093-10109.

Sun, et al., "Selection of Appropriate Biogas Upgrading Technology—a Review of Biogas Cleaning, Upgrading and Utilisation", Renewable and Sustainable Energy Reviews 51 (2015) 521-532.

Sun, et al., "Updates of Hydrogen Production from SMR Process in GREET". 2019.

Taylor, R., et al., "Options for a UK low carbon hydrogen standard: Final Report", Department for Business, Energy & Industrial Strategy, E4tech, May 2021 (this document uploaded in two parts).

U.S. Climate Change Technology Program—Technology Options for the Near and Long Term, Methane Emissions from Energy and Waste, "Conversion of Landfill Gas to Alternative Uses", section 4.1.2, Nov. 2003, pp. 153-155.

Union Calendar No. 94, 117th Congress 1st Session, H.R. 5376 (Report No. 117-130) (2021).

Van Der Drift, "SNG: A New Biomass-Based Energy Carrier," Energy Research Centre of the Netherlands, Apr. 23, 2006, pp. 1-21.

Van Der Meijden et al. "Production of bio-methane from woody biomass", Energy Research Centre of the Netherlands, ECN-M-09-086, Jun. 2009, pp. 1-8.

Wang et al., "The Life-Cycle Analysis of Petroleum Fuels and Biofuels with GREET", Argonne National Laboratory, Dec. 2016 (Access date: Jun. 2, 2020), in 32 pages. URL: https://ww2.arb.ca.gov/sites/default/files/classic/fuels/lcfs/lcfs_meetings/12132016wang.pdf.

Wang, "Low Carbon Steam Reforming-Based Hydrogen Production", Access date: Feb. 6, 2021, in 33 pages. URL: https://www.gasliquids.com/wp-content/uploads/2020_Hydrogen-Production-Using-Steam-Methane-Reforming.pdf.

Wismann, et al., "Electrified methane reforming: a compact approach to greener industrial hydrogen production", Science (2019), 364 (6442), 756-759.

Worley, et al., "Biomass Gasification Technology Assessment," National Renewable Energy Laboratory, Nov. 2012, pp. 1-358.

Yang et al., "Cost and Lifecycle Greenhouse Gas Implications of Integrating Biogas Upgrading and Carbon Capture Technologies in Cellulosic Biorefineries", Environ. Sci. Technol., 2020, 54, 12810-12819.

Zhou et al., "Life-cycle Greenhouse Gas Emissions of Biomethane and Hydrogen Pathways in the European Union", https://theicct.

(56) References Cited

OTHER PUBLICATIONS org/publication/life-cycle-greenhouse-gas-emissions-of-biomethane-and-hydrogen-pathways-in-the-european-union/ Access Date: Nov. 7, 2022.

International Search Report and Written Opinion dated Jun. 29, 2022 for PCT Application No. PCT/CA2022/050612, filed Apr. 21, 2022.

\* cited by examiner

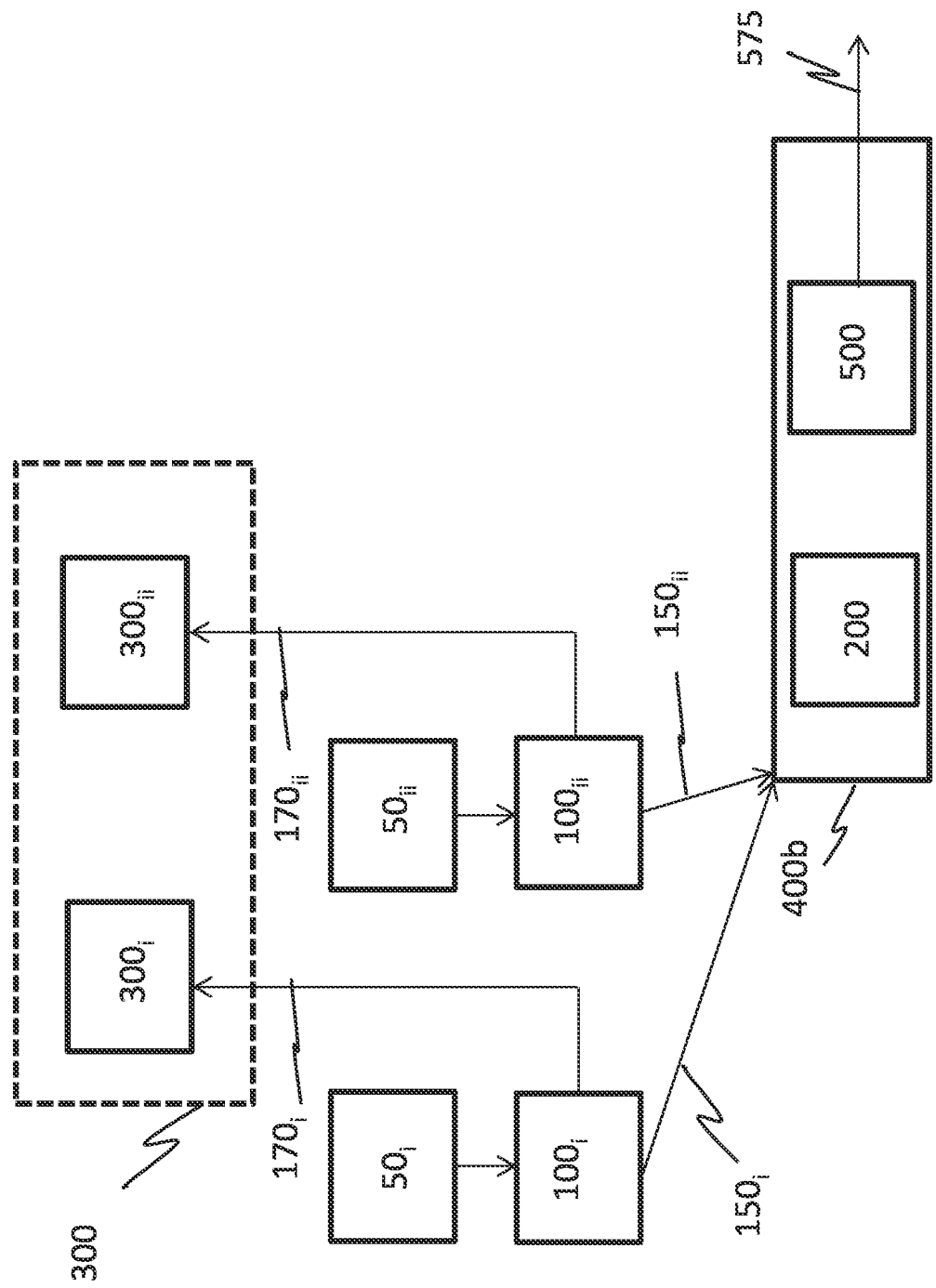

PROCESS AND SYSTEM FOR PRODUCING FUEL

TECHNICAL FIELD

The present disclosure relates to a process and/or system for producing fuel and/or product(s), and in particular, to a process and/or system for producing fuel and/or products(s) having renewable content that includes carbon capture and storage of carbon dioxide from biogas.

BACKGROUND

Hydrogen is largely produced from the processing of fossil fuels. For example, hydrogen is often produced from the steam methane reforming (SMR) of natural gas or the gasification of coal. Unfortunately, the production of hydrogen from fossil fuels is associated with significant greenhouse gas (GHG) emissions, and in particular, with significant carbon dioxide ($CO_2$) emissions.

One approach to reduce the GHG emissions associated with hydrogen production is to use carbon capture and storage (CCS). CCS may, for example, involve capturing $CO_2$ emissions and storing them underground in suitable geological formations (i.e., carbon sequestration). In integrating CCS with hydrogen production from fossil fuels, the fossil based $CO_2$ produced during the hydrogen production is captured and stored in order to prevent it from being released to the atmosphere, thereby reducing GHG emissions of the process (e.g., a reduction of about 80-90%).

Another approach to reduce the GHG emissions associated with hydrogen production is to use biomass rather than fossil fuels as feedstock. Such hydrogen, may for example, be produced from the gasification or pyrolysis of biomass, or by reforming biogas produced by the anaerobic digestion of biomass. Any $CO_2$ derived from biomass and produced during such processing is biogenic. As the release of biogenic $CO_2$ to the atmosphere simply returns to the atmosphere carbon that was recently fixed by photosynthesis, biogenic $CO_2$ is generally considered to be carbon neutral (e.g., its release does not result in an increase in net GHG emissions). Accordingly, such hydrogen production can have reduced GHG emissions. In addition, such hydrogen (e.g., produced by reforming biogas) may be considered renewable hydrogen.

In integrating CCS with hydrogen production from biomass, where biogenic $CO_2$ produced during the hydrogen production is captured and stored, there is the potential for so-called "negative emissions." Negative emissions can be the basis for BECCS, which stands for bioenergy with carbon capture and storage. For example, in some cases, BECCS, which is a group of technologies that combine extracting bioenergy from biomass with CCS, can be viewed as a process where biomass (e.g., plants) is used to extract $CO_2$ from the atmosphere, the biomass is processed to produce bioenergy (e.g., heat, electricity, fuels) while releasing $CO_2$, and the $CO_2$ produced during the processing is captured and stored such that there is there is a transfer of $CO_2$ from the atmosphere to storage.

While BECCS is increasing discussed as a means to decrease $CO_2$ emissions and/or $CO_2$ concentrations in the atmosphere, some potential challenges that may hinder its success include 1) energy intensive biomass supply chains, 2) low energy conversion efficiencies, and/or 3) high costs (e.g., incentives and/or funding may be required). For example, the cost of BECCS may be largely limited by the cost of CCS. Since the cost of CCS is typically scale sensitive, and since the capture of $CO_2$ is often considered to be one of most expensive parts of CCS, BECCS has been generally considered for applications where the $CO_2$ emissions are relatively pure and/or can be captured from a large point source. Some potential applications of BECCS have been identified as power stations wherein biomass is combusted (e.g., where biogenic $CO_2$ generated from the combustion process is captured and stored), biogas upgrading processes (e.g., where $CO_2$ separated from the biogas captured and stored), and ethanol production processes (e.g., where $CO_2$ produced by fermentation of corn grain is captured and stored).

It has also been proposed to combine CCS with hydrogen production from upgraded biogas, wherein at least a portion of the biogenic $CO_2$ produced from hydrogen production is captured and stored. Such processes benefit from established technologies for capturing $CO_2$ from hydrogen production (e.g., which can be a large point source). In some cases, the captured and stored $CO_2$ can be accounted for as negative $CO_2$ emission.

SUMMARY

The present disclosure relates to producing fuel and/or product in a process that uses hydrogen and/or includes the production of hydrogen, wherein a carbon intensity or lifecycle greenhouse gas emissions of at least a portion of the fuel and/or product is reduced by the capture and storage of carbon dioxide from biogas used to produce feedstock for the process (e.g., for hydrogen production). Accordingly, CCS can be incorporated into the process even when the hydrogen production is conducted in areas that do not practically support CCS.

In accordance with one aspect of the instant invention there is provided a method for producing fuel, the method comprising: sourcing at least two upgraded biogases, each of the at least two upgraded biogases produced in a process comprising: a) collecting biogas comprising methane and carbon dioxide, b) capturing carbon dioxide from the collected biogas and producing upgraded biogas, and c) providing the captured carbon dioxide for storage; providing the at least two upgraded biogases for use as feedstock at a facility that has hydrogen production, the hydrogen production comprising methane reforming; and, producing a fuel having renewable content in a fuel production process that uses hydrogen produced from the hydrogen production as a feedstock, wherein the captured carbon dioxide provided in step (c) of each of the processes is stored and reduces the carbon intensity of the fuel. In some aspects, the fuel production comprises hydrogenating crude oil derived liquid hydrocarbon with the renewable hydrogen to produce the fuel. In some aspects, the fuel production comprises hydrogenating a renewable feedstock selected from renewable oil and renewable fat to produce the fuel. In some aspects, the fuel is selected from gasoline, diesel, and jet fuel. In some aspects, the fuel is aviation fuel. In some aspects, carbon dioxide captured from one of the processes is provided for storage at a separate location than carbon dioxide captured from another of the processes. In some aspects, step (c) of at least one of the processes comprises providing the captured carbon dioxide for geological sequestration. In some aspects, step (c) of at least one of the processes comprises providing the captured carbon dioxide for enhanced oil recovery. In some aspects, step (c) of at least one of the processes comprises providing the captured carbon dioxide for sequestration in concrete. In some aspects, step (c) of at least one of the processes comprises compressing the captured carbon dioxide and injecting the captured carbon dioxide into a carbon dioxide distribution system configured to transport the captured carbon dioxide to storage. In some aspects, step (b) of at least one of the processes comprises capturing the carbon dioxide using carbon dioxide capture selected from cryogenic separation, membrane separation, and absorption with amine solvent. In some aspects, step (b) of at least one of the processes comprises capturing at least 70% of the carbon dioxide originally present in the biogas. In some aspects, feedstock for the hydrogen production comprises the least two upgraded biogases and fossil based natural gas. In some aspects, the process does not include storing carbon dioxide produced from the hydrogen production. In some aspects, at least one of the at least two upgraded biogases is derived from organic waste. In some aspects, at least one of the at least two upgraded biogases is derived from manure, the manure selected from swine manure and dairy manure. In some aspects, at least one of the at least two upgraded biogases is derived from landfill gas. In some aspects, at least one of the at least two upgraded biogases is transported to the hydrogen plant using a natural gas distribution system.

In accordance with one aspect of the instant invention there is provided a process for producing fuel having renewable content, the process comprising: a) providing at least two biogas streams, each of the at least two biogas streams comprising methane and carbon dioxide; b) processing each of the at least two biogas streams, the processing comprising carbon capture and biogas upgrading, the processing of each of the at least two biogas streams producing upgraded biogas and captured carbon dioxide; c) providing the upgraded biogas produced from the processing of the at least two biogas streams for use as a feedstock at a facility that has hydrogen production, the hydrogen production comprising methane reforming, the hydrogen production producing hydrogen used as a feedstock in a fuel production process, the fuel production process producing fuel having renewable content; and d) storing the captured carbon dioxide produced from the processing of the at least two biogas streams, thereby preventing the captured carbon dioxide, or an equal quantity of carbon dioxide displaced by the captured carbon dioxide, from being released to the atmosphere, and reducing a carbon intensity of the fuel.

In accordance with one aspect of the instant invention there is provided a process for producing fuel having renewable content, the process comprising: sourcing at least two upgraded biogases, each of the at least two upgraded biogases produced in a biogas production process comprising: a) collecting biogas comprising methane and carbon dioxide, b) capturing carbon dioxide from the collected biogas and producing upgraded biogas, c) providing the captured carbon dioxide for storage; providing the at least two upgraded biogases for use as feedstock at a facility that has hydrogen production, the hydrogen production comprising methane reforming; and producing a fuel having renewable content in a fuel production process that uses hydrogen produced from the hydrogen production as a feedstock; and storing the captured carbon dioxide provided in step (c) of each of the biogas production processes, thereby reducing a carbon intensity of the fuel.

In accordance with one aspect of the instant invention there is provided a method for producing one or more products, the method comprising: providing a plurality of upgraded biogases, each upgraded biogas in the plurality produced in a respective process comprising: a) collecting biogas comprising methane and carbon dioxide, b) removing at least a portion of the carbon dioxide from the biogas and producing upgraded biogas; providing at least a portion of each upgraded biogas from the plurality as feedstock for hydrogen production, the hydrogen production comprising methane reforming, renewable hydrogen produced from the hydrogen production used for producing the one or more products; and storing carbon dioxide removed in b) from at least two of the processes, thereby preventing the removed carbon dioxide, or an equal quantity of carbon dioxide displaced by the removed carbon dioxide, from being released to the atmosphere, the storing reducing lifecycle GHG emissions of the one or more products.

In accordance with one aspect of the instant invention there is provided a method for producing one or more products, the method comprising: providing a plurality of upgraded biogases for producing renewable hydrogen via methane reforming, the renewable hydrogen for use in producing the one or more products, each upgraded biogas in the plurality produced in a respective process comprising: a) collecting biogas comprising methane and carbon dioxide, b) removing at least a portion of the carbon dioxide from the biogas and producing upgraded biogas; reducing lifecycle greenhouse gas emissions of the one or more products, the reducing comprising carrying out a plurality of carbon capture and storage processes, each of the carbon capture and storage processes in the plurality storing at least a portion of the carbon dioxide removed in step b) of one of the biogas production processes.

In accordance with one aspect of the instant invention there is provided a method for producing one or more products, the method comprising: producing a plurality of upgraded biogases, each upgraded biogas in the plurality produced in a respective process comprising: a) feeding biogas comprising methane and carbon dioxide into biogas upgrading, the biogas produced by anaerobic digestion, the biogas upgrading removing at least a portion of the carbon dioxide from the biogas and producing upgraded biogas, and b) processing digestate from the anaerobic digestion; providing at least a portion of each upgraded biogas from the plurality as feedstock for hydrogen production, the hydrogen production comprising methane reforming, renewable hydrogen produced from the hydrogen production used for producing the one or more products; and storing carbon dioxide removed in a) and carbon-containing material produced in b) from at least two of the biogas production processes, the storing reducing lifecycle GHG emissions of the one or more products.

In accordance with one aspect of the instant invention there is provided a method for reducing a lifecycle greenhouse gas emissions of one or more products, the one or products produced in a production process that consumes hydrogen, the hydrogen produced in a hydrogen production process that comprises methane reforming, the method comprising: providing a plurality of upgraded biogases, at least a portion of each of the upgraded biogases in the plurality provided as feedstock for the hydrogen production or a production process comprising the hydrogen production, each of the upgraded biogases produced in a respective process comprising: a) collecting biogas produced from anaerobic digestion of biomass, the biogas comprising methane and carbon dioxide, and b) removing at least a portion of the carbon dioxide from the biogas and producing upgraded biogas, storing carbon-containing material obtained or derived from at least two of the respective processes as part one or more carbon capture and storage processes, thereby reducing the lifecycle greenhouse gas emissions of the one or more products, the carbon-containing material comprising carbon dioxide.

BRIEF DESCRIPTION OF THE DRAWINGS

FIG. 3 is a simplified process flow diagram according to an embodiment of the invention.

DETAILED DESCRIPTION

Figure 1:
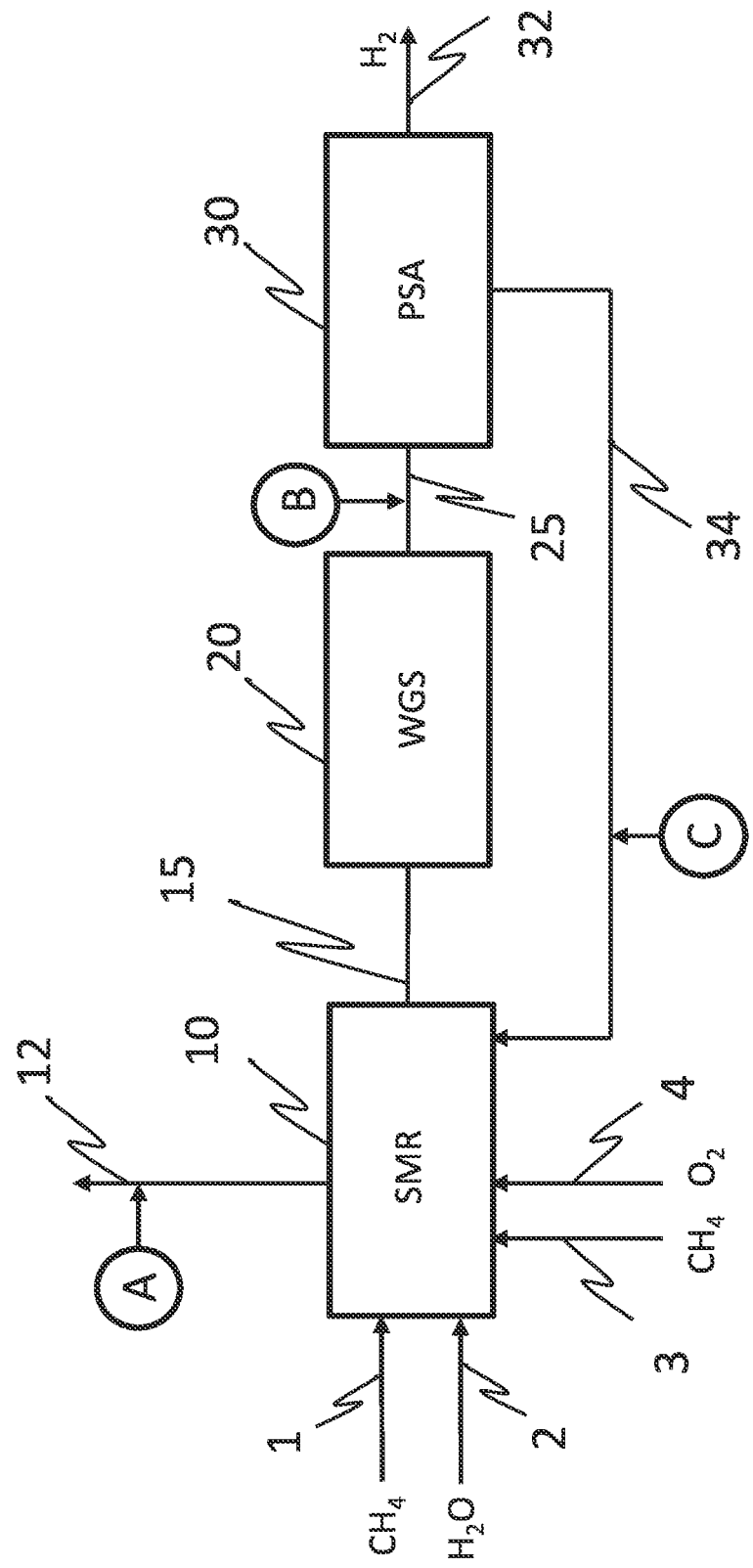
FIG. 1 is a simplified process flow diagram of one embodiment of an SMR based hydrogen plant.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or constituents of biogas, includes partial removal. The terms "cause" or "causing", as used herein, may include arranging or bringing about a specific result (e.g., a withdrawal of a gas), either directly or indirectly, or to play a role in a series of activities through commercial arrangements such as a written agreement, verbal agreement, or contract. The term "associated with", as used herein with reference to two elements (e.g., a fuel credit associated with the transportation fuel), is intended to refer to the two elements being connected with each other, linked to each other, related in some way, dependent upon each other in some way, and/or in some relationship with each other. The terms "first", "second", etc., may be used to distinguish one element from another, and these elements should not be limited by these terms. The term "plurality", as used herein, refers to two or more. The term "providing" as used herein with respect to an element, refers to directly or indirectly obtaining the element and/or making the element available for use. The terms "upstream" and "downstream", as used herein, refer to the disposition of a step/stage in the process with respect to the disposition of other steps/stages of the process. For example, the term upstream can be used to describe to a step/stage that occurs at an earlier point of the process, whereas the term downstream can be used to describe a step/stage that occurs later in the process. Unless defined otherwise, all technical and scientific terms used herein have the same meanings as commonly understood by one of ordinary skill in the art.

The term "biomass", as used herein, refers to organic material originating from plants, animals, or micro-organisms (e.g., including plants, agricultural crops or residues, municipal wastes, and algae). Biomass is a renewable resource, which can be naturally replenished on a human timescale, and which can be used to produce bioenergy, biofuels (e.g., biogas), and/or renewable products (e.g., chemicals).

The term "biogas", as used herein, refers to a gas mixture that contains methane produced from biomass. While biogas is predominately produced from the anaerobic digestion (AD) of biomass, it is also possible to produce biogas from the gasification of biomass. For example, the gasification of biomass may produce syngas, which may be cleaned up, and methanated. When produced from the anaerobic digestion of biomass, raw biogas typically includes methane ($CH_4$), carbon dioxide ($CO_2$), and can contain water ($H_2O$), nitrogen ($N_2$), hydrogen sulfide ($H_2S$), ammonia ($NH_3$), oxygen ($O_2$), volatile organic compounds (VOCs), and/or siloxanes, depending up its source. The term biogas, as used herein, can refer to raw biogas, cleaned biogas, or upgraded biogas.

The term "raw biogas", as used herein, refers to biogas as obtained from its source (e.g., anaerobic digester or landfill) before it is treated to remove any chemical components (e.g., $CO_2$, $H_2O$, $H_2S$, $O_2$, $NH_3$, VOCs, siloxanes, and/or particulates). Raw biogas can be subjected to biogas cleaning to produce cleaned biogas or subjected to biogas upgrading to produce upgraded biogas.

The term "biogas cleaning", as used herein, refers to a process where biogas (e.g., raw biogas) is treated to remove one or more components (e.g., $H_2O$, $H_2S$, $O_2$, VOCs, siloxanes, and/or particulates), but does not remove a significant amount of $CO_2$ and/or $N_2$ (e.g., the calorific value of the biogas may not change significantly as a result of biogas cleaning).

The term "biogas upgrading", as used herein, refers to a process where biogas (e.g., raw or cleaned biogas) is treated to remove one or more components (e.g., $CO_2$, $N_2$, $H_2O$, $H_2S$, $O_2$, VOCs, siloxanes, and/or particulates), wherein the treatment is selected to increase the calorific value of the biogas. For example, biogas upgrading typically includes removing $CO_2$ and/or $N_2$. Biogas upgrading, which can include biogas cleaning, produces upgraded biogas. The term "upgraded biogas", as used herein, can refer to a partially purified biogas (i.e., requires further treatment in order to meet applicable specifications) or renewable natural gas (RNG). The term "upgraded biogas", as used herein, can refer to natural gas withdrawn from a distribution system that has been assigned environmental attributes associated with a corresponding amount of upgraded biogas that was injected into the natural gas distribution system (e.g., upgraded biogas that was transported as a fungible batch in a natural gas pipeline).

The term "renewable natural gas" or "RNG", as used herein, refers to biogas that has been upgraded to meet or exceed applicable natural gas pipeline specifications, meet or exceed applicable quality specifications for vehicle use (e.g., CNG specifications), and/or natural gas withdrawn from a natural gas distribution system that is associated with the environmental attributes of biogas injected into the natural gas distribution system (e.g., a gas that qualifies as RNG under applicable regulations). For example, the term RNG can refer to natural gas withdrawn from a distribution system that has been assigned environmental attributes associated with a corresponding amount of RNG, upgraded from biogas, that was injected into the natural gas distribution system. Pipeline specifications include specifications required for biogas for injection into a natural gas distribution system. Pipeline quality standards or specifications may vary by region and/or country in terms of value and units. For example, pipelines standards may require the RNG to have a $CH_4$ level that is at least 95% or have a heating value of at least 950 BTU/scf. The percentages used to quantify gas composition and/or a specific gas content, as used herein, are expressed as mol %, unless otherwise specified. More specifically, they are expressed by mole fraction at standard temperature and pressure (STP), which is equivalent to volume fraction.

The term "natural gas" or "NG", as used herein, refers a gas mixture rich in hydrocarbons, where the primary component is $CH_4$. The term "gas" or "gas mixture", as used herein, refers to a fluid that is gaseous at standard temperatures and pressures, unless indicated otherwise.

The term "environmental attributes", as used herein with regard to a specific material (e.g., biogas), refers to any and all attributes related to the material, including all rights, credits, benefits, or payments associated with the renewable nature of the material and/or the reduction in or avoidance of fossil fuel consumption or reduction in lifecycle GHG gas emissions associated with the use of the material. Some non-limiting examples of environmental attributes include verified emission reductions, voluntary emission reductions, offsets, allowances, credits, avoided compliance costs, emission rights and authorizations, certificates, voluntary carbon units, under any law or regulation, or any emission reduction registry, trading system, or reporting or reduction program for GHG gas emissions that is established, certified, maintained, or recognized by any international, governmental, or nongovernmental agency.

The terms "capturing and storing", as used herein with reference to $CO_2$, refers to capturing the $CO_2$ and storing the captured $CO_2$ to prevent the captured $CO_2$, or an equal quantity of $CO_2$ displaced physically by the captured $CO_2$, from being released to the atmosphere. Capturing the $CO_2$ can include removing $CO_2$ from a gas mixture (e.g., biogas, syngas) using any suitable separation technology, or if the $CO_2$ is relatively pure, capturing the $CO_2$ can simply refer to collecting the $CO_2$ (e.g., in a pipe). Storing the captured $CO_2$ can include sequestering it underground (e.g., trapping it in geological formations, such as saline aquifers, or using it for enhanced oil recovery (EOR)), or can include storing the captured $CO_2$ in one or more products (e.g., using the captured $CO_2$ as a resource to create valuable products such plastics, concrete, etc.). For example, "capturing and storing $CO_2$" can be part of one or more processes commonly referred to as "carbon capture and sequestration", "carbon capture and utilization" or CCU, or "carbon capture, utilization and storage" or CCUS. In general, capturing and storing $CO_2$ can also include compressing the captured $CO_2$ (e.g., to produce liquid $CO_2$ or for injection into a $CO_2$ distribution system) and transporting the captured $CO_2$ to storage (e.g., by vehicle and/or a $CO_2$ distribution system). As will be understood by those skilled in the art, it can be advantageous to store the captured $CO_2$ using a method recognized by the applicable regulatory authority for reducing GHG emissions and/or mitigating climate change.

The term "carbon intensity" or "CI" refers to the quantity of lifecycle GHG emissions, per unit of fuel energy, and is often expressed in grams of $CO_2$ equivalent emissions per unit of fuel (e.g., $gCO_2e$/MJ or $gCO_2e$/MMBTU). As will be understood by those skilled in the art, CI and/or lifecycle GHG emissions are often determined using Lifecycle Analysis (LCA), which identifies and estimates all GHG emissions in producing fuel and/or product, from the growing or extraction of raw materials, to the production of the fuel and/or product, through to the end use (e.g., well-to-wheel). Those skilled in the art will understand that CI values and/or lifecycle GHG emissions for a given fuel and/or product can be dependent upon the LCA methodology used (e.g., as required by the applicable regulatory authority). Methodologies for calculating CI values and/or lifecycle GHG emissions according to various regulatory bodies are well known in the art and can be readily calculated by those of ordinary skill in the art. The CI values recited herein are determined using the CA-GREET3.0 model (e.g., see, https://ww2.arb.ca.gov/resources/documents/lcfs-life-cycle-analysis-models-and-documentation), unless otherwise specified.

The present disclosure relates to producing fuel and/or product in a process (e.g., fuel production process) that uses hydrogen and includes carbon capture and storage, wherein the carbon capture and storage includes the carbon capture and storage of $CO_2$ removed from biogas (e.g., raw biogas).

Raw biogas produced from the anaerobic digestion of biomass can have a significant $CO_2$ content (e.g., about 35%), which reduces the calorific value of the biogas (i.e., relative to pure methane). As a result, the use of raw and/or cleaned biogas may be limited to power generation, co-generation, or producing heat for buildings. Alternatively, raw or cleaned biogas can be upgraded (e.g., to RNG) and used as a substitute for fossil based natural gas (e.g., used as a transportation fuel in the form of compressed RNG (bio-CNG) or liquefied RNG (bio-LNG)).

As a substitute for fossil based natural gas, upgraded biogas (e.g., RNG) may be used to produce renewable hydrogen using any technology suitable for converting natural gas to hydrogen (e.g., methane reforming). Renewable hydrogen, which can be in gas or liquid form, is very versatile as it can be used as fuel, converted into electricity, and/or used as industrial feedstock (e.g., to produce fuel, fuel intermediates, or products). For example, renewable hydrogen can power fuel cell electric vehicles (FCEVs), which emit no tailpipe emissions other than water, can be run through a fuel cell to power the electricity grid, or can be used in oil refining, ammonia production, fertilizer production, methanol production, and/or steel production. As described herein, renewable hydrogen also can be used to produce fuels (e.g., liquid fuel such gasoline, diesel, and/or jet fuel) that are renewable and/or have renewable content.

Converting upgraded biogas (e.g., RNG) to renewable hydrogen by SMR is advantageous in that it exploits technology that is well established for natural gas. Unfortunately, compared to natural gas, supply of biogas may be limited, may fluctuate with the season, and/or may be from remote locations. While the relatively small scale and/or remote locations may be advantageous when the goal is to produce a grid of hydrogen refueling stations for FCEVs (e.g., where multiple geographically spaced small scale hydrogen plants can avoid transport and storage problems with hydrogen), such distributed hydrogen production cannot take advantage of economies of scale (e.g., SMR based hydrogen production is more economical when operated at a large scale), and thus is more expensive. Given the low value of raw biogas, the relatively small scale of many biogas plants, the cost of biogas upgrading, and/or the cost of SMR, it may be challenging to find facility owners willing to collect biogas and convert it to hydrogen, particularly since other uses of biogas are more economical.

It may be particularly challenging to find facility owners further willing to integrate CCS with such processes. Distributed carbon capture may be considered unfavorable compared to centralized large-scale carbon capture. For example, the cost of CCS is typically scale sensitive, and since distributed hydrogen production is generally small scale, the cost of CCS for distributed hydrogen production may be prohibitive. In addition, a lack infrastructure (e.g., $CO_2$ pipelines) and/or space-consuming $CO_2$ purification and capture equipment may be a deterrent for distributed CCS.

While large-scale CCS has been demonstrated for SMR plants that process fossil based natural gas, it is not cheap, and is not necessarily simple. For example, consider the hydrogen plant illustrated in FIG. 1. A stream of preheated natural gas 1 is desulfurized (not shown) and fed, along with steam 2, into the reactor tubes for the SMR 10, which contain the reforming catalyst. Streams of natural gas 3 and combustion air 4 are fed into the SMR burners, which provide the heat required for the endothermic reforming reaction. The syngas 15 produced from the SMR is fed to water gas shift (WGS) 20 to produce more hydrogen. The resulting syngas 25, which may also be referred to as shifted gas, is cooled (not shown) and purified using pressure swing adsorption (PSA) 30, which produces a stream enriched in hydrogen 32 and a purge stream 34. The purge stream 34, which may contain unconverted $CH_4$, Hz, $CO_2$, and/or CO, is fed back to SMR 10, where it is used to provide process heat for the SMR (e.g., fuel the SMR burners). More specifically, the purge stream 34 is combusted together with the stream of natural gas 3.

In the hydrogen production process illustrated in FIG. 1, there are two sources of $CO_2$, namely, $CO_2$ produced from the feedstock 1 for the SMR (e.g., $CO_2$ in the syngas 25), which can make up about 60% of the total $CO_2$ produced, and $CO_2$ produced from the fuel 3 for SMR (e.g., $CO_2$ in the flue gas 12), which can make up about 40% of the total $CO_2$ produced, depending upon the configuration of the hydrogen plant. In terms of capturing $CO_2$, there are various options of how and where the $CO_2$ may be captured, each with different energy requirements and/or yields. FIG. 1 identifies three possible options.

The first option, which is labelled A, captures $CO_2$ from the flue gas 12, and thus captures both $CO_2$ from the feedstock and $CO_2$ from the fuel (e.g., may capture up to about 90% of the total $CO_2$ produced). The second option, which is labelled B, captures $CO_2$ from the syngas 25, and thus captures only the $CO_2$ from the feedstock (e.g., about 60% of the $CO_2$). The third option, which is labelled C, captures $CO_2$ from the purge gas 34, and thus also captures only the $CO_2$ from the feedstock. While the first option theoretically can capture more $CO_2$ from the hydrogen production, capturing carbon dioxide from the syngas 25 (e.g., using vacuum pressure swing adsorption (VPSA) or an absorption amine unit) or from the purge gas 34 (e.g., using an activated amine process) may be more technically and/or economically feasible. For example, relative to the syngas 25, the flue gas may have a relatively low $CO_2$ concentration (e.g., relatively low partial pressure) and/or may be at a lower pressure (e.g., atmospheric). In addition, the flue gas may contain $N_2$ ($N_2$—$CH_4$ separations may be more challenging than $CO_2$—$CH_4$ separations).

In general, the SMR of fossil based natural gas to produce hydrogen can produce significant GHG emissions. While cooling of the syngas can allow heat recovery back into the process (e.g., steam generation and boiler feed water preheating), thereby preventing GHG emissions that would be associated with the heat, the resulting hydrogen can still have a high CI. For example, hydrogen produced from the SMR of fossil based natural gas, which is often referred to as "grey hydrogen," may have a CI of about 100 g$CO_2$e/MJ. When CCS is integrated with the SMR of fossil based natural gas, the resulting hydrogen it is often referred to as "blue hydrogen." As will be understood by those skilled in the art, the CI of blue hydrogen is dependent on both the hydrogen production and how much of the fossil based $CO_2$ is captured and stored. For example, in the case where only the $CO_2$ from the feedstock is captured and stored (i.e., not the flue gas), blue hydrogen may have a CI of about 45 g$CO_2$e/MJ.

As discussed herein, another approach to reduce the CI of hydrogen is to use a renewable feedstock (e.g., use RNG instead of fossil based natural gas), thereby producing renewable hydrogen. The CI of renewable hydrogen produced by the SMR of RNG can be dependent on the CI of the RNG, which can be dependent upon its source. For example, compared to the CI of fossil based natural gas, which can be about 80 g$CO_2$e/MJ, RNG produced from a landfill may have a CI of about 46 g$CO_2$e/MJ, whereas RNG produced from manure may have a CI of about −271 g$CO_2$e/MJ of $CH_4$ (e.g., as a result of avoided GHG emissions). Assuming that fossil based natural gas is used to fuel the SMR (e.g., fuel stream 3 is fossil based natural gas), the CI of renewable hydrogen produced by the SMR of landfill based RNG may be about 65 g$CO_2$e/MJ (e.g., higher than blue hydrogen). If this process is integrated with CCS, wherein only the $CO_2$ from the feedstock for SMR is captured and stored, the renewable hydrogen may have a CI of about 11 g$CO_2$e/MJ. Such calculations are discussed in further detail with regard to Table 1. For comparative purposes, the CI of compressed $H_2$ from electrolysis run with green electricity, which can be referred to as "green hydrogen", may be less than 10 g$CO_2$e/MJ.

The present disclosure relates to at least one process/system wherein at least a portion of the feedstock for hydrogen production and/or the fuel and/or product production is sourced from a plurality of biogas plants. Accordingly, the hydrogen production and/or fuel/product production can benefit from the economies of scale and/or higher efficiency. However, rather than relying on the capture and storage of $CO_2$ produced from hydrogen production, the carbon capture and storage is distributed (i.e., biogenic $CO_2$ is captured at a plurality of biogas plants).

While CCS at a plurality of biogas plants can be more expensive than CCS at a single hydrogen plant, there are various advantages and/or synergistic benefits of the process(es)/system(s) of instant disclosure. For example, it allows the benefits of CCS to accrue to hydrogen plants where CCS is not feasible (e.g., for economic reasons and/or technical reasons, such as extensive distances between the hydrogen plant and the storage site). Another advantage is that it can allow incremental transitioning, where upgraded biogas (associated with the distributed CCS) is co-processed with fossil based natural gas, thereby gradually increasing the production of hydrogen having a low CI. Advantageously, this can be achieved using existing hydrogen plants without modification. Yet another advantage is that it facilitates the aggregation of upgraded biogas from several locations (e.g., several biogas plants) and several CCS storage sites (e.g., basins) into one hydrogen production process.

One potential synergistic advantage of the process(es)/system(s) disclosure disclosed herein relates to capital efficiency. While the capital cost of distributed CCS from a plurality of biogas plants can be higher than the cost of CCS at a single hydrogen plant, the CI benefits of the capital for the distributed CCS accrues only to the upgraded biogas. In contrast, the CI benefits of the capital for CCS from centralized hydrogen production can accrue equally to all $H_2$ produced (e.g., the CCS can be conducted on both renewable and fossil based feedstocks, and thus can be conducted on a much larger scale). In circumstances where biofuels are treated differently, this can create special advantages.

Figure 2:
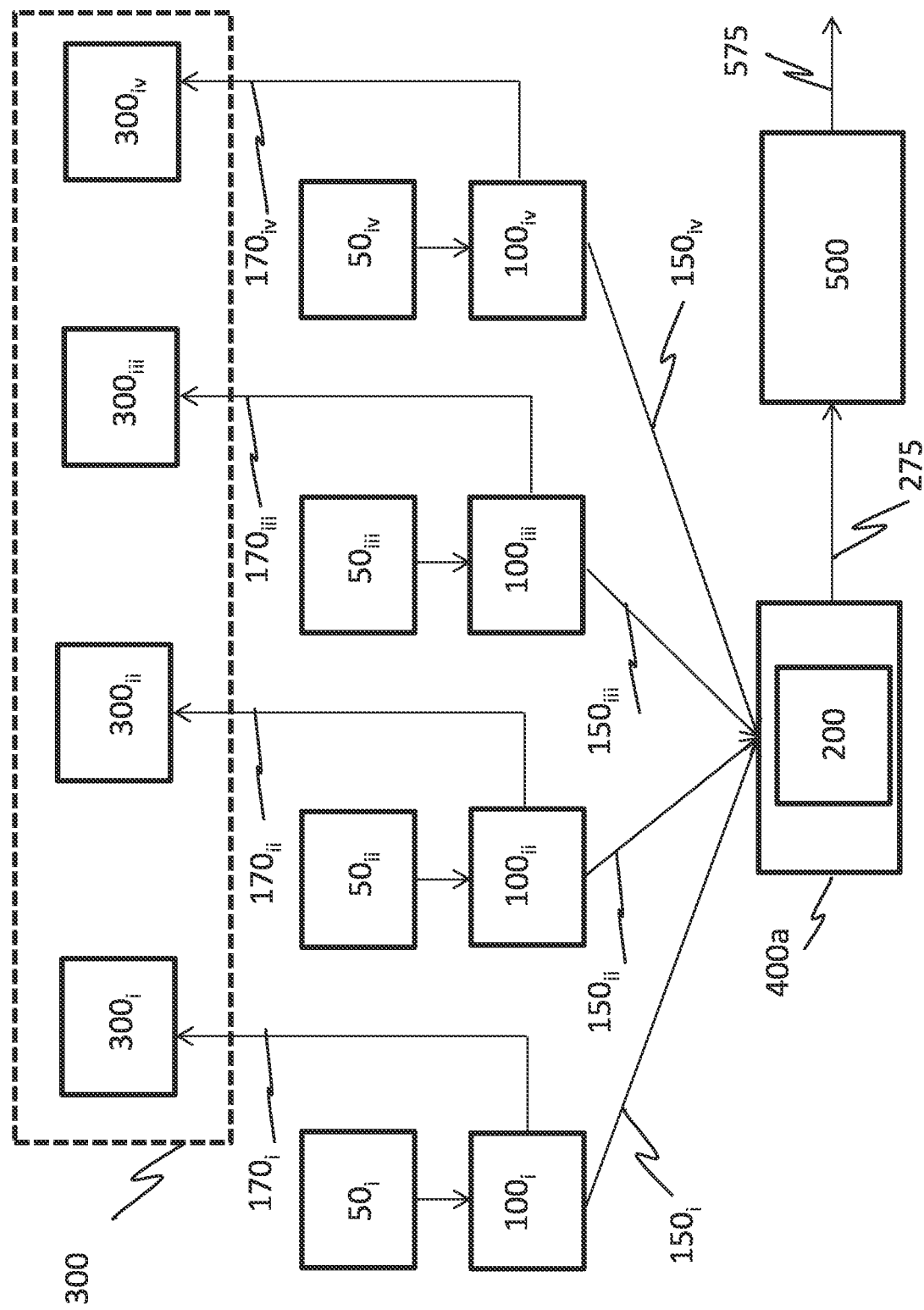
FIG. 2 is a simplified process flow diagram according to an embodiment of the invention.

Referring to FIG. 2, there is shown an embodiment of the disclosure. Biomass is converted to biogas via multiple biogas productions $50_i$, $50_{ii}$, $50_{iii}$, $50_{iv}$. For example, each of the multiple biogas productions $50_i$, $50_{ii}$, $50_{iii}$, $50_{iv}$ can include the anaerobic digestion of one or more feedstocks. In general, the feedstock for the multiple biogas productions $50_i$, $50_{ii}$, $50_{iii}$, $50_{iv}$ can be the same or different. For example, each of the multiple biogas productions $50_i$, $50_{ii}$, $50_{iii}$, $50_{iv}$, may be conducted at landfill or anaerobic digester. Each of the multiple biogas productions $50_i$, $50_{ii}$, $50_{iii}$, $50_{iv}$ produces biogas (e.g., raw biogas) that is treated in respective processing $100_i$, $100_{ii}$, $100_{iii}$, $100_{iv}$, to provide upgraded biogas $150_i$, $150_{ii}$, $150_{iii}$, $150_{iv}$, at least a portion of each provided to a facility 400a having hydrogen production 200. For example, at least part of the processing $100_i$, $100_{ii}$, $100_{iii}$, $100_{iv}$ may be conducted at a biogas plant (e.g., located close to the source of biogas) and may be transported to the facility that has hydrogen production 400a. Hydrogen production 200 converts at least a portion of the upgraded biogas (e.g., RNG) to renewable hydrogen (e.g., via SMR). The renewable hydrogen in the $H_2$ product 275 is used in a fuel and/or product production process 500 that produces the fuel/product 575 (e.g., a transportation fuel). In addition to biogas upgrading, the processing $100_i$, $100_{ii}$, $100_{iii}$, $100_{iv}$ also includes carbon capture wherein at least a portion of the $CO_2$ from each of the biogases (e.g., generated during anaerobic digestion) is captured. The captured $CO_2$ $170_i$, $170_{ii}$, $170_{iii}$, $170_{iv}$ is provided for storage 300.

In FIG. 2, the facility 400a having hydrogen production 200 is separate from the fuel and/or product production facility (e.g., is commercial hydrogen plant). In FIG. 3, the facility 400b having hydrogen production 200 is the fuel and/or product production facility.

In general, the upgraded biogas $150_i$, $150_{ii}$, $150_{iii}$, $150_{iv}$ may be transported to hydrogen production 200, the captured $CO_2$ $170_i$, $170_{ii}$, $170_{iii}$, $170_{iv}$ may be transported to storage 300, and/or the hydrogen product 275 may be transported to the fuel and/or product production facility, using any suitable mode of transportation, including transport by a commercial distribution system (e.g., pipeline) and/or vehicle (e.g., ship, rail car, and/or truck). For example, each of the upgraded biogases $150_i$, $150_{ii}$, $150_{iii}$, $150_{iv}$, each of the captured streams of $CO_2$ $170_i$, $170_{ii}$, $170_{iii}$, $170_{iv}$, and/or the hydrogen product 275 may be provided as segregated batch and/or a fungible batch. In one particularly advantageous embodiment, one or more of the upgraded biogases $150_i$, $150_{ii}$, $150_{iii}$, $150_{iv}$ is injected into a natural gas distribution system near the corresponding processing $100_i$, $100_{ii}$, $100_{iii}$, $100_{iv}$ and is withdrawn from the same natural gas distribution system for hydrogen production 200 (e.g., is transported as a fungible batch to the hydrogen plant and/or fuel and/or product production facility).

In general, the captured $CO_2$ $170_i$, $170_{ii}$, $170_{iii}$, $170_{iv}$ can be stored at one or more locations. For example, since the processing $100_i$, $100_{ii}$, $100_{iii}$, $100_{iv}$ may be conducted at different locations (e.g., different states or provinces), in some embodiments at least two of the captured streams $CO_2$ $170_i$, $170_{ii}$, $170_{iii}$, $170_{iv}$ are provided for storage in different geological formations. In one embodiment, all of the captured $CO_2$ $170_i$, $170_{ii}$, $170_{iii}$, $170_{iv}$ is stored in the same storage 300. In one embodiment, each of the captured $CO_2$ gases $170_i$, $170_{ii}$, $170_{iii}$, $170_{iv}$ is stored at respective storage sites $300_i$, $300_{ii}$, $300_{iii}$, $300_{iv}$. In one embodiment, at least one of the $CO_2$ gases $170_i$, $170_{ii}$, $170_{iii}$, $170_{iv}$ is used for CCSU, while another is used for CCS. In another example, all of the $CO_2$ gases $170_i$, $170_{ii}$, $170_{iii}$, $170_{iv}$ are provided for geological sequestration, but are sequestered in more than one geological formation (e.g., based on proximity of the storage to processing).

Although this process relies on multiple $CO_2$ capture steps, which are often considered to be energy-consuming steps, there are various advantages and/or synergetic benefits of using this process for producing fuel having renewable content and/or renewable hydrogen.

For example, compare the process discussed with reference to FIGS. 2 and 3 to the gasification of biomass. Biomass gasification may offer large scale centralized hydrogen production, facilitates collecting the biogenic carbon dioxide from one point source, and avoids some intermediate steps (e.g., the conversion of biomass to biogas and biogas upgrading). Nevertheless, there are challenges to hydrogen production via biomass gasification, many of which relate to the costs associated with capital equipment and biomass feedstocks. A facility producing 100 tonnes of hydrogen per day may be very large (e.g., require 1,350 dry tonnes of biomass feedstock per day), and thus may not be feasible based on regional supplies. Smaller facilities may be more feasible from a feedstock availability perspective but may drive up the capital expenditures. The cost of the biomass feedstocks can be dependent on costs for storage and transportation of the biomass, the latter of which may be dependent on the collection radius. Feedstock costs may be modest where agricultural residues can be collected and transported over short distances, but can be high when significant transport distances are involved, at least in part due to the low energy density of biomass.

Alternatively, compare the process discussed with reference to FIGS. 2 and 3 to the SMR of biogas, wherein biomass is transported to a centralized processing facility that conducts the anaerobic digestion, biogas upgrading, and hydrogen production (i.e., upgraded biogas is not transported). As with the gasification of biomass, the feedstock costs for such a process can be largely dependent on the storage and transportation of the biomass. When the feedstock has a large moisture content (e.g., manure or food waste) the transportation cost may be even higher.

In contrast, in the process illustrated in FIGS. 2 and 3, the upgraded biogas is transported to a facility having the hydrogen production 200. Transporting upgraded biogas over extended distances can be more cost efficient than transporting feedstock for anaerobic digestion and/or gasification. In particular, upgraded biogas such as RNG may be transported using any method suitable for transporting natural gas (e.g., a truck designed for transporting liquefied natural gas (LNG) or compressed natural gas (CNG), the latter of which is often transported at pressures above about 3600 psig (24.8 MPa)). Transporting the upgraded biogas as bio-LNG or bio-CNG allows more MJ to be delivered per truck (e.g., relative to biomass for gasification or anaerobic digestion) and/or can increase the collection radius for the renewable feedstock. Alternatively, or additionally, the upgraded biogas can be transported by pipeline (e.g., in a natural gas distribution system such as the US natural gas grid), where it is transported as a fungible batch.

Transporting the upgraded biogas via a natural gas distribution system is particularly advantageous. In particular, it is a cost effective method that uses existing infrastructure, and depending upon the applicable regulatory agency, may have only a small penalty (cost and/or GHG emissions) for transporting the upgraded biogas over extended distances. Accordingly, the collection zone for the renewable feedstock is not necessarily limited to the area around a centralized facility conducting anaerobic digestion, biogas upgrading, and hydrogen production, but rather can include any area that provides feedstock for biogas production, where the biogas production is near the natural gas distribution system or can be economically transported to an injection point of the natural gas distribution system. This can increase the area from which the feedstock is collected, thereby making more feedstock available for the process and increasing the feasible scale of the renewable hydrogen production and/or CCS. Transporting the upgraded biogas via a natural gas distribution system also advantageously facilitates the co-processing of renewable and non-renewable feedstock (e.g., upgraded biogas and fossil-based natural gas).

Coprocessing renewable and non-renewable feedstock can increase the possible scale of hydrogen production, can facilitate using existing hydrogen plant(s) configured to process natural gas, and/or can reduce operational complications associated with intermittent renewable feedstock supply (e.g., cold start-up times may be between about 15 and 24 hours). Accordingly, the costs of hydrogen production can be reduced.

Advantageously, providing multiple $CO_2$ capture steps (e.g., the disaggregation of $CO_2$ capture process) for $CO_2$ storage allows each capture process to be optimized for the $CO_2$ capture. For example, since biogas upgrading typically includes separating $CO_2$ from $CH_4$, many biogas upgrading technologies can include $CO_2$ capture, can be readily modified to include $CO_2$ capture, or may facilitate $CO_2$ capture, thereby reducing costs of the $CO_2$ capture.

Further details about the biogas production $50_i$, $50_{ii}$, $50_{iii}$, $50_{iv}$, the biogas processing $100_i$, $100_{ii}$, $100_{iii}$, $100_{iv}$, hydrogen production 200, capture and/or storage 300, and fuel/product production 500, are discussed below.

Biogas Production

In general, the multiple biogas productions $50_i$, $50_{ii}$, $50_{iii}$, $50_{iv}$ produce multiple biogases (i.e., each biogas production produces a respective biogas). Each biogas can be produced from any suitable biomass. For example, each biogas can be produced from the anaerobic digestion of any suitable feedstock. Anaerobic digestion, which refers to the biological breakdown of organic matter by anaerobic microorganisms, is typically conducted in anaerobic or low oxygen conditions, and may involve a series of microorganism types and processes (e.g., hydrolysis, acidogenesis, acetogenesis, and methanogenesis).

In one embodiment, one or more of the biogases is produced from the anaerobic digestion of a feedstock, where the feedstock is and/or comprises: (i) an energy crop (e.g., switchgrass, sorghum, etc.); (ii) residues, byproducts, or waste from the processing of plant material in a facility, or feedstock derived therefrom (e.g., sugarcane bagasse, sugarcane tops/leaves, corn stover, etc.); (iii) agricultural residues (e.g., wheat straw, corn cobs, barley straw, corn stover, etc.); (iv) forestry material; (v) pulp and paper residues; and/or (vi) municipal waste or components removed or derived from municipal waste. In one embodiment, the feedstock for the anaerobic digestion is or includes cellulosic and/or lignocellulosic material(s).

In one embodiment, one or more of the biogases is produced from the anaerobic digestion of "organic waste." Using organic waste as the feedstock for anaerobic digestion is particularly advantageous. Organic waste, may for example, include the organic fraction of municipal solid waste (MSW), sludge from a wastewater treatment plant (WWTP), manure from a livestock farm (e.g., a dairy or swine farm), or food or yard waste collected from households, restaurants, supermarkets, food-processing companies, schools, businesses, etc. In one embodiment, the feedstock for the anaerobic digestion is manure (e.g., swine or dairy) or other farm waste, the organic fraction of MSW, or agricultural residues (e.g., straw, stover, etc.).

The composition of biogas produced from each anaerobic digestion can be dependent upon the feedstock. For example, although biogas produced from anaerobic digestion generally has a $CH_4$ content between about 35% and 75% (e.g., about 60%) and a $CO_2$ content between about 15% and 65% (e.g., about 35%), the $CH_4$ content can tend towards the high end of this range when the feedstock is agricultural waste (e.g., between about 50% and 75%) and towards the low end of this range when the feedstock is the organic fraction of municipal solid waste (e.g., between about 25% and 65%). In addition to CHT and $CO_2$ biogas produced from anaerobic digestion may also include $N_2$, $H_2O$, $H_2S$, $NH_3$, VOCs, siloxanes, and/or particulates, in dependence upon its source. For example, biogas produced from a landfill often has a higher $N_2$ content than biogas produced in anaerobic digester. In one embodiment, each biogas has a $CH_4$ content between about 25% and 75% and a $CO_2$ content between about 15% and 65%, and the $CO_2$ and $CH_4$ make up at least 75% of the biogas by volume.

The anaerobic digestion of the feedstocks (e.g., solid or liquid) can be conducted in any suitable environment, including a natural environment (e.g., a landfill) or a controlled environment (e.g., an anaerobic digester). An anaerobic digester can be a holding tank, or another contained volume, such as a covered lagoon or sealed structure, configured to facilitate the breakdown of organic material by microorganisms under anaerobic or low oxygen conditions. Anaerobic digestion may be carried out in one or multiple anaerobic digesters connected in series and/or parallel, where each digester may be a single-stage or multi-stage digestion system, and/or may be designed and/or operated in a number of configurations including batch or continuous, mesophilic or thermophilic temperature ranges, and low, medium, or high rates. The term "anaerobic digester", as used herein, can refer to plurality of fluidly connected anaerobic digesters. The operation of an anaerobic digester may be dependent on nature of the organic matter fed to the anaerobic digester and/or the level of digestion required. The appropriate selection of operating parameters, including but not limited to residence time, temperature, pH, and/or the nutrients supplied, will be known to those skilled in the art. When conducted in one or more anaerobic digesters, the anaerobic digestion of biomass also produces a potentially usable digestate. Digestate refers to the material remaining after one or more stages of the anaerobic digestion (e.g., may refer to acidogenic digestate, methanogenic digestate, or a combination thereof). Digestate can include organic material not digested by the anaerobic microorganisms, by-products of the anaerobic digestion released by the microorganisms, and/or the microorganisms themselves. For example, the digestate can include carbohydrates, nutrients (such as nitrogen compounds and phosphates), other organics, and/or wild yeasts. The composition of digestate can vary depending on the biomass from which it is derived. Digestate often has both a solid and liquid component. A common use of digestate is as a soil conditioner, where it can provide nutrients for plant growth and/or displace the use of fossil-based fertilizers. In one embodiment, the digestate is processed to provide carbon-containing material that is stored as part of CCS. Processing of the digestate can include any type of processing, including but not limited to, solid liquid separations e.g., feeding it into a screw press), heating, combustion, pyrolysis, hydrothermal treatment, etc.

In one embodiment, each of the biogases is produced from a single source (e.g., a landfill or anaerobic digester). In one embodiment, one or more of the biogases is produced from multiple sources (e.g., one or more landfills and/or one or more anaerobic digesters).

Biogas Upgrading

In general, at least part of each processing $100_i$, $100_{ii}$, $100_{iii}$, $100_{iv}$ includes biogas upgrading. Biogas upgrading, which can be conducted in a biogas plant situated at or close the biogas production, refers to a process where biogas is purified in one or more stages to provide upgraded biogas. Biogas upgrading, which increases the calorific value of the biogas, typically provides a $CH_4$-rich gas having a $CH_4$ content of at least 90%. In one embodiment, the upgraded biogases have a $CH_4$ content of at least 90%, at least 91%, at least 92%, at least 93%, at least 94%, at least 95%, at least 96%, at least 97%, or at least at least 98%. It can be particularly advantageous to produce upgraded biogas having a $CH_4$ content that facilitates transporting the upgraded biogas as CNG, or that facilitates injection into a natural gas distribution system. In one embodiment, the biogas upgrading produces RNG. In one embodiment, the biogas upgrading produces biogas having a $CH_4$ content of at least 95%. In one embodiment, the biogas upgrading produces biogas having a heating value of at least 950 BTU/ft$^3$.

Biogas upgrading can be conducted using any suitable technology or combination of technologies that can separate $CH_4$ from one or more non-methane components in the biogas (e.g., $CO_2$, $N_2$, $H_2S$, $H_2O$, $NH_3$, $O_2$, VOCs, siloxanes, and/or particulates). For example, biogas upgrading technologies are often based on absorption, adsorption, membrane separation, and/or cryogenic separation. As will be understood by those skilled in the art, the technology used for the biogas upgrading can be dependent up the composition of the biogas and the desired purity of the upgraded biogas.

As biogas typically has a significant $CO_2$ content, biogas plants often include at least one system for separating $CH_4$ from $CO_2$. Some examples of technologies that can remove $CO_2$ from biogas include, but are not limited to, absorption (e.g., water scrubbing, organic physical scrubbing, chemical scrubbing), adsorption (e.g., pressure swing adsorption (PSA)), membrane separation (e.g., $CO_2$ selective membranes based on polyimide, polysulfone, cellulose acetate, polydimethylsiloxane), and cryogenic separation.

While some $CO_2$ removal systems may remove one or more other non-methane components in addition to $CO_2$ (e.g., $N_2$, $H_2S$, $H_2O$, $NH_3$, $O_2$, VOCs, siloxanes, and/or particulates), biogas plants often include one or more other systems (e.g., dehydration units, $H_2S$ removal units, $N_2$ rejection units, etc.). For example, some $CO_2$ removal systems require that the biogas be cleaned upstream of $CO_2$ removal (e.g., remove impurities that can negatively affect the $CO_2$ removal unit. Alternatively, or additionally, the biogas can be cleaned and/or upgraded downstream of $CO_2$ removal. In general, the non-methane components can be removed by any combination of chemical and/or physical technologies, in one or more stages. For example, $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). In some cases, one stage may remove more than one non-methane component. For example, in some cases, some $H_2S$ may also be removed during the water removal step.

In general, the biogas upgrading can be conducted close to the biogas source (e.g., at a biogas plant at the landfill site or near the anaerobic digester) and/or at a centralized biogas plant (e.g., which receives raw, cleaned, or partially purified biogas from multiple sources). For example, a centralized biogas plant may be connected to one or more anaerobic digesters (e.g., each at a separate farm) via a biogas pipeline and/or grid. Alternatively, or additionally, the centralized biogas plant may receive biogas from one or more biogas sources by vehicle (e.g., see U.S. Pat. No. 10,760,024). In one embodiment, each biogas processing $100_i$, $100_{ii}$, $100_{iii}$, $100_{iv}$ is conducted on biogas from a single biogas source. In one embodiment, at least one biogas processing $100_i$, $100_{ii}$, $100_{iii}$, $100_{iv}$ is conducted at a centralized processing plant that receives biogas from multiple biogas sources (e.g., multiple farms).

Each of the upgraded biogases $150_i$, $150_{ii}$, $150_{iii}$, $150_{iv}$ is transported to a facility having hydrogen production (e.g., to a stand-alone hydrogen plant or to a production facility having at least one hydrogen production process). As each upgraded biogas may be relatively pure (e.g., have a $CH_4$ content greater than about 92%), it may be transported using methods used to transport natural gas. For example, if the biogas is upgraded to RNG it can be transported in a CNG tanker (e.g., at a pressure of about 3600 psig) and/or transported by pipeline (e.g., a natural gas distribution system such as the US natural gas grid). In some cases, upgraded biogas that does not meet pipeline standards can be mixed with another gas (e.g., propane or fossil based natural gas) in order to facilitate injection into the natural gas distribution system.

In general, when upgraded biogas is transported by pipeline, it is transferred as a fluid (e.g., in gaseous or liquid form), and may be provided as a segregated batch or a fungible batch. The term "batch", as used herein, refers to a certain amount of the gas (e.g., energy delivered) and does not imply or exclude an interruption in the production and/or delivery.

When upgraded biogas is transported as a fungible batch in a natural gas distribution system, a quantity of the upgraded biogas (e.g., in MJ) is injected into the natural gas distribution system, where it can comingle with non-renewable natural gas, and an equivalent quantity of gas (e.g., in MJ) is withdrawn at another location (i.e., as long as there is a physical link between the injection point and the withdrawal point). The transfer or allocation of the environmental attributes of the upgraded biogas injected into the natural gas distribution system to gas withdrawn at a different location is typically recognized. Accordingly, the withdrawn gas can be recognized as the transported upgraded biogas and/or can qualify as RNG under applicable regulations (e.g., even though the withdrawn gas may not contain actual molecules from the original biomass and/or contains methane from fossil sources). Such transport may be carried out on a displacement basis, where transactions within the natural gas distribution system involve a matching and balancing of inputs and outputs. Typically, the direction of the physical flow of gas is not considered. Establishing that a gas is recognized as and/or qualifies as RNG (e.g., originates from renewable sources) under applicable regulations can depend on whether the gas is transported by truck or by pipeline and the practices and requirements of the applicable regulatory agency, where such practices may include, for example, the use of chain of custody accounting methods such as identity preservation, book-and-claim, and/or mass balance.

Transporting the upgraded biogas via a natural gas grid is particularly advantageous as it facilitates transporting the renewable feedstock anywhere where the grid delivers without significant additional cost (e.g., financially and/or GHG emissions). In one embodiment, the upgraded biogas is transported to a facility having hydrogen production, at least in part, via a natural gas distribution system. In one embodiment, each of the upgraded biogases is transported to a facility having hydrogen production, at least in part, by vehicle. In one embodiment, each of the upgraded biogases is transported to a facility having hydrogen production, at least in part, using a transportation system.

The term "transportation system", as used herein with reference to an element (e.g., natural gas or $CO_2$ or $H_2$), refers to a system configured to transport the element, and/or a fungible element, by a distribution system and/or vehicle. For example, a transportation system can include a mobile pressure vessel configured to be transported by vehicle (e.g., truck, rail car, ship). The term "distribution system", as used herein with reference to an element (e.g., natural gas or $CO_2$ or $H_2$), refers to a system configured to transport the element, and/or a fungible element, in one or more interconnected pipes (e.g., by pipeline). For example, a natural gas distribution system such as the US natural gas grid can be used to transport natural gas and/or upgraded biogas.

Hydrogen Production

In general, the hydrogen production may be conducted at one or more hydrogen plants. The term "hydrogen plant", as used herein, refers to a system or combination of systems primarily used for hydrogen production. The term "renewable hydrogen", as used herein, refers to hydrogen produced using biogas (e.g., upgraded biogas and/or RNG). For example, the term "renewable hydrogen" can refer to hydrogen produced by methane reforming a feed withdrawn from a natural gas distribution system, when at least a portion of the withdrawn feed is recognized as and/or qualifies as RNG under applicable regulations.

In general, the hydrogen production may use any suitable technology known in the art that can convert one or more of the upgraded biogases and/or natural gas to hydrogen. Examples of technologies that may be suitable include, but are not limited to, steam methane reforming (SMR), autothermal reforming (ATR), partial oxidation (PDX), and dry methane reforming (DMR). SMR, ATR, and DMR, which are types of catalytic reforming, may operate by exposing natural gas to a catalyst at high temperature and pressure to produce syngas. PDX reactions, which include thermal partial oxidation reactions (TPDX) and catalytic partial oxidation reactions (CPDX), may occur when a sub-stoichiometric fuel-oxygen mixture is partially combusted in a reformer. PDX also may be referred to as oxidative reforming. For purposes herein, the term "methane reforming" may refer to SMR, ATR, DMR, or PDX.

Of the various types of methane reforming, SMR is the most common. In SMR, which is an endothermic process, methane is reacted with steam under pressure in the presence of a catalyst to produce carbon monoxide (CO) and $H_2$ according to the following reaction:

$$CH_4 + H_2 + \text{heat} \rightarrow CO + 3H_2 \quad (1)$$

Referring to the hydrogen plant in FIG. 1, this reaction may occur in the SMR reactor tubes, which contain the reforming catalyst. Without being limiting, the catalyst may be nickel-based, the operating pressure may be between 200 psig (1.38 MPa) and 600 psig (4.14 MPa), and the operating temperature may be between about 450 to 1000° C. The heat required for the catalytic reforming of Eq. 1 can be provided by the combustion in the SMR burners (e.g., the combustion chamber may surround the reformer tubes in which the reaction is conducted).

The syngas produced from Eq. (1) may be further reacted in the WGS 20. The WGS is based on the water gas shift reaction, wherein carbon monoxide is converted to carbon dioxide and hydrogen:

$$CO + H_2O \rightarrow CO_2 + H_2 + \text{small amount of heat} \quad (2)$$

Providing WGS downstream of SMR increases the yield of Hz, and thus is commonly included in hydrogen production. For example, in addition to Hz, the syngas produced from the SMR may have a $CO_2$ content between about 7-10%, a CO content between about 12-19%, and a $CH_4$ content between about 2-6%, whereas the syngas produced from the WGS may have a $CO_2$ content between about 15-16%, a CO content between about 4-5%, and a $CH_4$ content between about 3-4%.

The gas produced from methane reforming (e.g., the syngas 25) is subjected to a hydrogen purification, wherein $H_2$ is separated from CO, $CO_2$, and/or $CH_4$ in one or more stages to produce a hydrogen product (e.g., containing at least 80% hydrogen). For example, in one embodiment, the hydrogen purification produces an enriched hydrogen stream having a hydrogen content of at least 90, 92, 94, 96, 98, 99, or 99.5%. In one embodiment, the hydrogen purification produces an enriched hydrogen stream having a hydrogen content of at least 99.9%. Without being limiting, some examples of suitable hydrogen purification technologies include, but are not limited to: a) absorption, b) adsorption, c) membrane separation, d) cryogenic separation, and e) methanation. Some examples of absorption systems that may be suitable include, but are not limited to, a monoethanolamine (MEA) unit or a methyl-diethanolamine (MDEA) unit. A MEA unit may include one or more absorption columns containing an aqueous solution of MEA at about 30 wt %. The outlet liquid stream of solvent may be treated to regenerate the MEA and separate $CO_2$. Some examples of adsorption systems that may be suitable include, but are not limited to, systems that use adsorbent bed (e.g., molecular sieves, activated carbon, active alumina, or silica gel) to remove impurities such as $CH_4$, $CO_2$, CO, $N_2$, and/or water from the syngas gas. For example, hydrogen purification systems that are based on PSA are commonly used for hydrogen plants, as such systems produces a purge gas that can be recycled to fuel the SMR burners, thereby improving energy efficiency (e.g., see FIG. 1). In one embodiment, hydrogen purification uses vacuum PSA system (VPSA). Some examples of membranes systems that may be suitable include, but are not limited to, $H_2$ selective membranes. A hydrogen purification unit that is based on cryogenic separation may cool the syngas gas down to temperatures where the impurities condense or sublimate and can be separated as a liquid or a solid fraction, while the hydrogen accumulates in the gas phase. For example, cryogenic separations may use temperatures below −10° C. or below −50° C. Methanation is a catalytic process that can be conducted to convert the residual carbon monoxide and/or carbon dioxide in the syngas to methane. For example, see equation 3.

$$CO + 3H_2 \rightarrow CH_4 + H_2 \quad (3)$$

Since the methanation reaction consumes hydrogen, a hydrogen purification unit that includes a methanation may include $CO_2$ removal prior to methanation.

In general, hydrogen production is well known and those skilled in the art will understand that the hydrogen plant(s) may use any suitable technology and/or have any suitable configuration. For example, the hydrogen production may be based on any suitable methane reforming technology combined with any suitable hydrogen purification. With specific regard to FIG. 1, those skilled in the art will understand that each of the SMR unit 10 and WGS unit 20 may include a single reactor or multiple reactors (e.g., the WGS unit 20 may include a high temperature WGS reactor (e.g., 350° C.) followed by a low temperature WGS reactor (e.g., 200° C.)), that the SMR reactor(s) may be top-fired reformers, side-fired reformers, bottom-fired reformers, etc., that the SMR reformer may be downstream of a purification unit to remove sulfur, chloride, olefin, and/or other compounds that may be detrimental to the SMR reforming catalysts, or that the SMR reformer may be downstream a pre-reforming unit, which allows a higher inlet feed temperature with minimal risk of carbon deposition. Those skilled in the art will also understand that although a steam methane reformer may be referred to as a "methane reformer," typically they can convert any of the hydrocarbons present in the natural gas to syngas (i.e., not just the methane).

In the above-described embodiments, the feedstock for the hydrogen production process contains at least a portion of one or more of the upgraded biogases (e.g., RNG), which can be transported to the facility containing the hydrogen production (e.g., at least one hydrogen plant) by vehicle and/or as a fungible batch via a natural gas distribution system. In each embodiment, the feedstock may contain only the upgraded biogas or may contain both upgraded biogas and fossil based gas such as natural gas (e.g., the hydrogen can be produced by coprocessing renewable and non-renewable methane). When the feed contains both upgraded biogas and fossil based gas (e.g., natural gas or refinery gas), the quantity of renewable hydrogen produced can be determined using the renewable fraction of the feedstock (based on energy).

In the above-described embodiments, the feedstock for the renewable hydrogen process contains at least a portion of one or more of the upgraded biogases. However, in some embodiments, a portion of one or more of the upgraded biogases is fed to the combustion zone of the methane reformer (e.g., to the SMR burners). Since combusting upgraded biogas simply returns to the atmosphere carbon that was recently fixed by photosynthesis, and thus is considered relatively benign, this can reduce GHG emissions from the SMR furnace (e.g., compared to using fossil-based methane). Accordingly, the CI of renewable hydrogen could be reduced. While it may be advantageous to sacrifice some of the upgraded biogas for fuel in order to improve the GHG balance of the hydrogen production and/or fuel/product production process, this reduces the yield of renewable hydrogen and/or the yield of renewable content of the fuel(s)/product(s) produced. Accordingly, there may be a compromise between increasing the yield of renewable hydrogen/renewable content and decreasing the lifecycle GHG emissions, for a given quantity of upgraded biogas. In certain embodiments, low-carbon electricity such as renewable electricity is used to provide heat for the methane reforming (e.g., for SMR). Low-carbon electricity refers to electricity generated in a process that does not emit significant amounts of fossil-based carbon dioxide and/or is produced from renewable energy sources. Without being limiting, low-carbon electricity can include electricity produced using nuclear power, hydropower, solar power, wind power, geothermal power, wave power, tidal power, or electricity produced from the combustion of a low-carbon energy source (e.g., biomass, biogenic syngas, or hydrogen) or of a fossil-based energy source with CCS. In certain embodiments, heat required for the SMR is generated using renewable electricity (i.e., electricity produced using renewable energy sources such as hydropower, solar power, wind power, geothermal power, wave power, tidal power, etc.). In certain embodiments, the low-carbon electricity is generated from gasification of agricultural and/or solid waste. In general, any suitable technology known in the art that can use electricity to produce a sufficient amount of heat for at least part of the methane reforming can be used. The low-carbon electricity can produce the heat for methane reforming directly (e.g., to power resistive or inductive heaters that provide the heat directly for the methane reforming) and/or indirectly (e.g., using a heat storage medium and/or heat transfer fluid). In certain embodiments, the methane reformer (e.g., SMR) is an electrically heated methane reformer (e.g., electrically heated SMR), wherein the heat that would have been generated with conventional fired burners is replaced with electrically generated heat. Such methane reformers are generally configured such that there is no flue gas, and thus there are no carbon emissions associated with the flue gas (e.g., carbon emissions of hydrogen production may be reduced by 20-50% relative to the conventional fired SMR).

Carbon Capture and Storage

In general, at least part of each processing $100_i$, $100_{ii}$, $100_{iii}$, $100_{iv}$ includes carbon capture, wherein at least a portion of the $CO_2$ from the biogas produced (e.g., generated during anaerobic digestion) is captured. The capture of $CO_2$ from each biogas produced can be conducted using any suitable technology or combination of technologies that can capture $CO_2$ for storage. As the $CO_2$ may be part of a gas mixture (e.g., biogas, syngas, flue gas, etc.), the $CO_2$ capture can include and/or depend upon the separation of $CO_2$ from one or more other gas components in a gas mixture. Technology that may be suitable for separating $CO_2$ from one or more other gas components in a gas mixture includes, but is not limited to, absorption, adsorption, membrane separation, and cryogenic separation.

The $CO_2$ from each of the biogases (e.g., generated during anaerobic digestion) can be captured upstream of biogas upgrading, as part of biogas upgrading, and/or from a tail gas produced from biogas upgrading. For example, since biogas upgrading can include steps where $CO_2$ is separated from $CH_4$, such steps can be part of the $CO_2$ capture process, or can facilitate the $CO_2$ capture process, thereby reducing capital and operating costs. Biogas upgrading, which typically focuses on providing a relatively pure product stream (e.g., greater than 95% $CH_4$), can produce a tail gas that contains $CO_2$ separated from the $CH_4$ in addition to other non-methane components separated from the $CH_4$. For example, biogas upgrading units based on absorption, adsorption, or membrane separation, can produce a $CO_2$ rich tail gas that is too impure for $CO_2$ storage and/or transport without further purification and/or upstream removal of one or more components. However, in some cases, biogas upgrading (e.g., based on cryogenic separation), can yield both relatively pure $CH_4$ (e.g., greater than about 95% $CH_4$) and relatively pure $CO_2$ (e.g., greater than about 95% $CO_2$). While cryogenic biogas upgrading may require upstream biogas cleaning, it advantageously can provide the $CO_2$ is a form that facilitates transport by vehicle and/or a $CO_2$ distribution system (e.g., can provide the $CO_2$ in liquid or solid form).

In one embodiment, at least one of the processing steps $100_i$, $100_{ii}$, $100_{iii}$, $100_{iv}$ includes a separate $CO_2$ removal step for the $CO_2$ capture (i.e., separate from the biogas upgrading). For example, in one embodiment, a separate $CO_2$ separation is conducted on the tail gas from biogas upgrading to provide a $CO_2$ product that is sufficiently pure for $CO_2$ storage and/or transport. In another embodiment, a separate $CO_2$ separation is conducted upstream of biogas upgrading to provide a $CO_2$ product that is sufficiently pure for $CO_2$ storage and/or transport.

In one embodiment, the biogas upgrading is conducted in stages and at least one stage of the biogas upgrading is a $CO_2$ capture step.

In one embodiment, the $CO_2$ capture step is integrated with the biogas upgrading. For example, in one embodiment, the biogas upgrading is selected to and/or modified to provide a $CO_2$ product suitable for geological storage and/or transport by a $CO_2$ distribution system (e.g., after dehydration and compression). In general, this may be achieved by selecting suitable separation technology and/or modifying the configuration of the system (e.g., removing one or more components upstream of the $CO_2$ separation). For example, in one embodiment, cryogenic $CO_2$ capture is part of biogas upgrading. When cryogenic separation is used as part of biogas upgrading, the biogas may be cleaned (e.g., to remove $H_2S$ and $H_2O$) and then subjected to a cryogenic separation that provides relatively pure $CO_2$ (e.g., >95% $CO_2$) while also providing a relatively pure $CH_4$ (e.g., >95% $CH_4$) and $N_2$ (if present).

Storage of $CO_2$ captured from the biogases can be conducted using any suitable technology or combination of technologies. For example, carbon storage technologies, which are well known in the art, can sequester $CO_2$ in geological formations (i.e., subsurface formations). Suitable geological formations, which can occur in onshore or offshore settings, are often configured such that $CO_2$ injected therein, is trapped. Appropriate storage of the $CO_2$ can reduce GHG emissions and/or mitigate climate change. The level of GHG reduction achieved may be dependent on whether it is all biogenic, the applicable regulatory authority, the permanence of the storage, and/or whether its use displaces the use of fossil fuel products. In one embodiment, the captured. $CO_2$ from one or more of the biogases is sequestered in at least one geological formation. For example, in one embodiment the captured $CO_2$ from one or more of the biogases is sequestered in a saline aquifer or is sequestered in an oil/natural gas reservoir as part of enhanced oil recovery (EOR)). In one embodiment, the captured $CO_2$ from one or more of the biogases is stored in concrete. In one embodiment, storage of the captured $CO_2$ from one or more of the biogases permanently displaces fossil based $CO_2$ emissions.

The purity of the $CO_2$ required for storage can be dependent upon the selected storage and/or selected mode of transportation, if applicable. For example, for geological sequestration and/or EOR, where the $CO_2$ is often transported, at least in part, via a $CO_2$ distribution system (e.g., pipeline), the $CO_2$ content should be as high as possible (e.g., at least about 95%). However, for some applications (e.g., bauxite residue carbonation, etc.) lower $CO_2$ contents may be suitable. In addition to a minimum $CO_2$ content, the $CO_2$ provided for storage and/or transport may have limits on the maximum amount of $H_2O$, $H_2S$, CO, $CH_4$, $N_2$, Ar, $H_2$, etc.

In general, when the $CO_2$ is captured far from storage, the process includes transporting the captured $CO_2$ to storage (e.g., by vehicle and/or a $CO_2$ distribution system). In order to transport $CO_2$ for storage, the $CO_2$ typically requires significant compression and/or cooling. When $CO_2$ is transported by vehicle (e.g., truck, ship, rail car) it is often transported as a liquid (e.g., a pressure of about 290 psig and a temperature of about −20° C., or a pressure of about 100 psig and a temperature of about −50° C.). When $CO_2$ is transported by a $CO_2$ distribution system (e.g., a $CO_2$ pipeline) it is often transported as a supercritical fluid (critical point is ~31° C., ~1070 psig). For example, many $CO_2$ pipelines are operated between about 1250 psig and about 2200 psig, or higher. In some embodiments, the collected $CO_2$ is also stored locally at a relatively high pressure (e.g., ~1600 psig) prior to transport by pipeline. In general, the $CO_2$ can be compressed to the desired pressure using a gas compressor, or alternatively, the collected $CO_2$ can be liquefied at a lower pressure using a refrigeration system (e.g., 235 psig) and then pumped to the desired pressure. In one embodiment, the process produces a compressed stream of relatively pure $CO_2$ (e.g., at least 95% $CO_2$). In one embodiment, the $CO_2$ is transported to storage, at least in part, as a fungible batch using a $CO_2$ distribution system.

The $CO_2$ captured from the multiple biogas upgrading processes can be stored together or separately (e.g., in the same geological formation or in different geological formations). In general, how and where the captured $CO_2$ is stored may be dependent upon the closest storage site. In one embodiment, the $CO_2$ captured from one or more of the biogases is, at least in part, transported using a $CO_2$ distribution system.

In one embodiment, at least 50% of the $CO_2$ from each of one or more of the biogases is captured and stored. In one embodiment, at least 55%, at least 60%, at least 65%, at least 70%, at least 75%, at least 80%, at least 85%, at least 90% of the $CO_2$ from each of one or more of the biogases is captured and stored.

In certain embodiments, the carbon intensity and/or lifecycle GHG emissions of the fuel/product(s) is further reduced by storing carbon containing material obtained or derived from the biogas production/biogas upgrading. For example, in certain embodiments, digestate from anaerobic digestion of the biomass is provided for storage as part of CCS. In certain embodiments, the digestate is treated prior to CCS. For example, digestate can be subjected to a hydrothermal liquefaction to provide a bio-oil that can be sequestered. In some cases, the sequestration method is selected to prevent biodegradation of the material and/or trap GHGs in the event of biodegradation. In some cases, the material is treated in a process to reduce the potential for biodegradation. The amount of carbon obtained or derived from the digestate and provided as part of CCS can be expressed as kg C per $m^3$ (dry weight). Advantageously, storing a liquid or solid by-product produced from the process as part of CCS can further reduce the carbon intensity of the hydrogen produced and/or a fuel or product produced from the hydrogen.

Fuel or Product Production

In general, the process produces fuel and/or product (e.g., having renewable content) using renewable hydrogen. In one embodiment, the process produces fuel. In one embodiment, the fuel is methanol. In one embodiment, the fuel is gasoline, diesel, and/or jet fuel. In one embodiment, the fuel is an aviation fuel. In one embodiment, the fuel is a transportation fuel. In one embodiment, the fuel is a liquid transportation fuel. In one embodiment, the process produces one or more products (e.g., the renewable hydrogen is used as an industrial feedstock to produce one or more fuels and/or chemical products). In one embodiment, the renewable hydrogen is used to produce ammonia (e.g., in a Haber-Bosch process). In the Haber-Bosch process, which is well-known to those skilled in the art, nitrogen is converted to ammonia in a process conducted under high temperatures and pressures with a metal catalyst. Ammonia has an important role in the agricultural industry for production of fertilizers. Ammonia may also be used as a fuel and/or an energy carrier for energy storage and transportation. In one embodiment, the renewable hydrogen is used to produce fertilizer. Using the upgraded biogas and/or renewable hydrogen to produce fuel and/or product can provide the fuel and/or product with renewable content and/or can reduce the lifecycle GHG emissions of the fuel and/or product, particularly when the upgraded biogas and/or renewable hydrogen has a low CI attributed to CCS.

In general, the fuel and/or product may be produced by processing the upgraded biogas and/or renewable hydrogen with one or more other renewable feedstocks and/or one or more non-renewable feedstocks. When the process produces a fuel from the co-processing of renewable and non-renewable feedstocks, the fuel can have renewable content (e.g., be a partially renewable fuel). The term "renewable content", as used herein, refers the portion of the fuel(s)/product(s) that is recognized and/or qualifies as renewable (e.g., a biofuel) under applicable regulations. The quantification of the renewable content can be determined using any suitable method and is typically dependent upon the applicable regulations.

In one embodiment, the renewable hydrogen is used in the hydroprocessing (e.g., hydrocracking and/or hydrotreating) of crude-oil derived liquid hydrocarbon such that the renewable hydrogen is incorporated into a crude-oil derived liquid hydrocarbon to produce gasoline, diesel, and/or jet fuel having renewable content (e.g., see U.S. Pat. Nos. 8,658,026, 8,753,854, 8,945,373, 9,040,271, 10,093,540, 10,421,663, and 10,723,621, 10,981,784). In this embodiment, use of the renewable hydrogen can produce gasoline, diesel, and/or jet fuel having renewal content. Advantageously, such fuels can replace and/or be used with non-renewable gasoline, diesel, and/or jet fuel without affecting performance and/or operation (e.g., are drop-in fuels). Further advantageously, such fuels can be produced at existing oil refineries using existing equipment. The term "crude oil derived liquid hydrocarbon", as used herein, refers to any carbon-containing material obtained and/or derived from crude oil that is liquid at standard ambient temperature and pressure. The term "crude oil", as used herein, refers to petroleum extracted from geological formations (e.g., in its unrefined form). Crude oil includes liquid, gaseous, and/or solid carbon-containing material from geological formations, including oil reservoirs, such as hydrocarbons found within rock formations, oil sands, or oil shale. In one embodiment, the renewable hydrogen is used in the hydroprocessing (e.g., hydrocracking and/or hydrotreating) of crude-oil derived liquid hydrocarbon to produce aviation fuel having renewable content. This embodiment is particularly advantageous as it could help decarbonize commercial air travel and/or extend the life of older aircraft types by lowering their carbon footprint.

In one embodiment, the renewable hydrogen is used in the hydroprocessing (e.g., hydrocracking and/or hydrotreating) of renewable fats and/or oils (e.g., algae, jatropha, tallows, camelina, pyrolysis oil produced from biomass, etc.) to produce renewable gasoline, diesel, and/or jet fuel. This embodiment is particularly advantageous as the resulting fuel can be fully renewable and have a reduced CI (i.e., relative to an analogy process where the hydrogen is produced from fossil based natural gas).

In general, the renewable hydrogen can be used in any suitable fuel and/or product production process. For example, in one embodiment, the renewable hydrogen is used in a Fischer-Tropsch type process to produce a liquid transportation fuel. In one embodiment, the renewable hydrogen and biogenic carbon dioxide are subjected to a gas fermentation to produce an alcohol such as ethanol.

In general, the renewable hydrogen may be produced at a commercial hydrogen plant or at a hydrogen plant at the production facility. In both cases, the renewable hydrogen may be provided for fuel/product production via a $H_2$ distribution system (e.g., a $H_2$ pipeline or local $H_2$ pipe system) as a fungible batch. More specifically, the renewable hydrogen may be allocated for the desired use (e.g., a specific fuel production process or a specific hydroprocessing unit). The term "allocating", as used herein in respect of a particular element, refers to designating the element for a specific purpose.

Carbon Intensity and/or Fuel Credits

In general, the carbon intensity and/or lifecycle GHG emissions of the fuel and/or product having renewable content is relatively low as a result of the use of renewable hydrogen and/or storage of captured $CO_2$ 170$_i$, 170$ii$, 170$_{iii}$, 170$_{iv}$ (i.e., low relative to fuel produced by an analogous process using hydrogen produced using fossil based natural gas or an analogous process where the biogenic $CO_2$ 170$_i$, 170$ii$, 170$_{iii}$, 170$_{iv}$ is not stored). Advantageously, when the process produces fuel, the renewable content attributed to the use of renewable hydrogen and/or the low CI attributed to storing the captured $CO_2$ 170$_i$, 170$ii$, 170$_{iii}$, 170$_{iv}$ can facilitate the generation of fuel credits.

Fuel credits are used to incentivize renewable fuels, often in the transportation sector. For example, fuel credits can be used to demonstrate compliance with some government initiative, standard, and/or program, where the goal is to reduce GHG emissions (e.g., reduce CI in transportation fuels as compared to some baseline level related to conventional petroleum fuels) and/or produce a certain amount of biofuel (e.g., produce a mandated volume or a certain percentage of biofuels). The target GHG reductions and/or target biofuel amounts may be set per year or for a given target date. Some non-limiting examples of such initiatives, standards, and/or programs include the Renewable Fuel Standard Program (RFS2) in the United States, the Renewable Energy Directive (RED II) in Europe, the Fuel Quality Directive in Europe, the Renewable Transport Fuel Obligation (RTFO) in the United Kingdom, and/or the Low Carbon Fuel Standards (LCFS) in California, Oregon, or British Columbia).

The term "fuel credit", as used herein, refers to any rights, credits, revenues, offsets, GHG gas rights, or similar rights related to carbon credits, rights to any GHG gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. A fuel credit can be a certificate, record, serial number or guarantee, in any form, including electronic, which evidences production of a quantity of fuel meeting certain life cycle GHG emission reductions relative to a baseline (e.g., a gasoline baseline) set by a government authority. Non-limiting examples of fuel credits include RINs and LCFS credits. A Renewable Identification Number (or RIN), which is a certificate that acts as a tradable currency for managing compliance under the RFS2, may be generated for each gallon of biofuel (e.g., ethanol, biodiesel, etc.) produced. A Low Carbon Fuel Standard (LCFS) credit, which is a certificate which acts as a tradable currency for managing compliance under California's LCFS, may be generated for each metric ton (MT) of $CO_2$ reduced.

In general, the requirements for generating or causing the generation of fuel credits can vary by country, the agency, and or the prevailing regulations in/under which the fuel credit is generated. In many cases, fuel credit generation may be dependent upon a compliance pathway (e.g., predetermined or applied for) and/or the biofuel meeting a predetermined GHG emission threshold. For example, with regard to the former, the RFS2 categorizes biofuel as cellulosic biofuel, advanced biofuel, renewable biofuel, and biomass-based diesel. With regard to the latter, to be a renewable biofuel under the RFS2, corn ethanol should have lifecycle GHG emissions at least 20% lower than an energy-equivalent quantity of gasoline (e.g., 20% lower than the 2005 EPA average gasoline baseline of 93.08 $gCO_2e$/MJ). In low carbon-related fuel standards, biofuels may be credited according to the carbon reductions of their pathway. For example, under California's LCFS, each biofuel is given a CI score indicating their GHG emissions as grams of $CO_2$ equivalent per megajoule (MJ) of fuel, and fuel credits are generated based on a comparison of their emissions reductions to a target or standard that may decrease each year (e.g., in 2019, ethanol was compared to the gasoline average CI of 93.23 $gCO_2e$/MJ), where lower CIs generate proportionally more credits. In one embodiment, the fuel produced is a transportation fuel, and a fuel credit is generated or is caused to be generated. In one embodiment, the transportation fuel and/or renewable content has lifecycle GHG emissions that are at least 20% less than the lifecycle GHG emissions of a gasoline baseline using EPA methodology, preferably at least 50% or 60% less.

With respect to renewable hydrogen produced according to the instant disclosure, it can be advantageous for the CI of the hydrogen to be as low as possible, particularly when the hydrogen is used as a fuel or to produce a fuel, so that more valuable fuel credits can be generated. When the process produces a fuel from the co-processing of renewable and non-renewable feedstocks, the CI is measured for the resulting product from each of the co-processed feedstocks (i.e., there is a different CI for each the renewable and non-renewable feedstocks). In one embodiment, the process includes producing hydrogen associated with one or more producer credits.

EXAMPLE

Referring to Table 1, there is shown a list of estimated GHG emission values for hydrogen produced by various processes. As summarized in Table 2, these processes produce: 1) grey hydrogen from the SMR of natural gas with no CCS; 2) blue hydrogen from the SMR of natural gas with CCS (i.e., where the $CO_2$ is captured from the feedstock); 3) renewable hydrogen labelled "RH" from the SMR of RNG with no CCS; 4) renewable hydrogen labelled "RH+$CCS_{H2}$" from the SMR of RNG with CCS (i.e., where the $CO_2$ is captured from the feedstock only); 5) renewable hydrogen labelled "RH+$CCS_{H2}$+$CCS_{BG}$" from the SMR of RNG with CCS (i.e., where the $CO_2$ is captured from the feedstock and from the biogas); and 6) renewable hydrogen labelled "RH+$CCS_{BG}$" from the SMR of RNG with CCS (i.e., where the $CO_2$ is captured from the biogas only).

For each process, it was assumed that the fuel for the SMR burners is fossil based natural gas and that the feedstock for the methane reforming is RNG produced from landfill gas (i.e., is upgraded landfill gas). In order to compare the different processes, which can use different feedstocks, the emissions for the hydrogen production were split into the contributions from the feedstock (i.e., upstream emissions) and from the hydrogen production. Each emission (positive number) and emission credit (negative number) is an estimation based on one or more published values and/or determined using stoichiometry. For example, the feedstock emissions of 10 $gCO_2e$/MJ of $H_2$ for natural gas and 35 $gCO_2e$/MJ of $H_2$ for landfill gas are estimated from the CA-GREET 3.0 model. The feedstock emission credit of –42 $gCO_2e$/MJ of $H_2$, which is a net credit at least partially based on theoretical calculations, assumes that the emissions for CCS of the biogas is 5 $gCO_2e$/MJ of $H_2$. For the hydrogen production, emissions from the combustion of fuel for the SMR burners is assumed to be 28 $gCO_2e$/MJ of $H_2$, electricity is assumed to be 2 $gCO_2e$/MJ of $H_2$, and emissions from the conversion of the feedstock to syngas is assumed to be 60 $gCO_2e$ per MJ of $H_2$. Assuming all of the $CO_2$ from the feedstock is captured and stored, and if the CCS process from hydrogen production results in 5 $gCO_2e$/MJ of $H_2$ of emissions, the $CCS_{H2}$ process provides a net credit of –55 $gCO_2e$/MJ of $H_2$.

TABLE 1

GHG Emission Values, in $gCO_2e$/MJ of $H_2$, for various SMR based $H_2$ production processes

| | Feedstock | | Hydrogen Plant | | | | |
|---|---|---|---|---|---|---|---|
| Process | Feedstock | Feedstock $CO_2$ capture | Fuel Combustion | Feedstock conversion | Electricity | Hydrogen Plant $CO_2$ capture | CI |
| Grey $H_2$ | 10 | | 28 | 60 | 2 | | 100 |
| Blue $H_2$ | 10 | | 28 | 60 | 2 | –55 | 45 |
| RH | 35 | | 28 | | | 2 | 65 |

TABLE 1-continued

GHG Emission Values, in gCO$_2$e/MJ of H$_2$,
for various SMR based H$_2$ production processes

| | Feedstock | | Hydrogen Plant | | | | |
|---|---|---|---|---|---|---|---|
| Process | Feedstock | Feedstock CO$_2$ capture | Fuel Combustion | Feedstock conversion | Electricity | Hydrogen Plant CO$_2$ capture | CI |
| RH + CCS$_{H2}$ | 35 | | 28 | | 2 | −55 | 11 |
| RH + CCS$_{H2}$ + CCS$_{BG}$ | 35 | −42 | 28 | | 2 | −55 | −31 |
| RH + CCS$_{BG}$ | 35 | −42 | 28 | | 2 | | 24 |

TABLE 2

Summary of the various SMR based H$_2$ production processes

| Process | Description | Feedstock | CO$_2$ capture |
|---|---|---|---|
| 1 | Grey H$_2$ | Natural Gas | None |
| 2 | Blue H$_2$ | Natural Gas | Yes - Syngas |
| 3 | Renewable H$_2$ (RH) | RNG (landfill) | None |
| 4 | Renewable H$_2$ and CCS$_{H2}$ | RNG (landfill) | Yes - Syngas only |
| 5 | Renewable H$_2$ and CCS$_{H2}$ and CCS$_{BG}$ | RNG (landfill) | Yes - Syngas and upstream |
| 6 | Renewable H$_2$ and CCS$_{BG}$ | RNG (landfill) | Yes - Upstream only |

While the GHG emission values in Table 1 are estimations provided for comparative purposes, they do appear reasonable. For example, Table 1 lists the CI of grey hydrogen as 100 gCO$_2$e/MJ, which is within a published range of 94.8 to 101.4 g CO$_2$e/MJ. With regard to the CI of blue hydrogen, which Table 1 lists as 45 gCO$_2$e/MJ (with CCS of about 60% of the total CO$_2$ produced), some published values are 19.6 gCO$_2$e/MJ (with CCS of about 90% of the total CO$_2$ produced) and 34.5 gCO$_2$e/MJ (with CCS of about 80% of the total CO$_2$ produced).

As evident from Table 1, simply using RNG as a feedstock for hydrogen production, using RNG as a feedstock for hydrogen production and capturing CO$_2$ from the hydrogen production, or using RNG as a feedstock for hydrogen production and capturing CO$_2$ from the biogas, does not necessarily produce hydrogen having a negative CI, and can produce hydrogen having a higher CI than green hydrogen (e.g., which can be less than 10 gCO$_2$e/MJ).

However, as evident from Table 1, using RNG as a feedstock for hydrogen production and capturing CO$_2$ from the biogas does produce hydrogen having a lower CI than blue hydrogen, without the challenges of capturing and storing CO$_2$ from hydrogen production. Moreover, it produces renewable hydrogen. When renewable hydrogen having a relatively low CI is used in a fuel and/or product production process, the fuel and/or product produced can have renewable content, and the renewable content can have a relatively low CI (i.e., relative to the analogous process without storing the CO$_2$ from the biogas). Accordingly, the process(es) disclosed herein can be used to produce fuel having renewable content and a relatively low CI without CCS of CO$_2$ from hydrogen production.

Of course, the above embodiments have been provided as examples only. It will be appreciated by those of ordinary skill in the art that various modifications, alternate configurations, and/or equivalents will be employed without departing from the scope of the invention. For example, although the instant disclosure provides a process that provides renewable hydrogen and/or fuel and/or product having renewable content, with a relatively low CI without CCS of CO$_2$ from the hydrogen production, and although this is generally advantageous, in some embodiments, the CO$_2$ from hydrogen production is also captured and stored (e.g., from the syngas and/or the flue gas). Accordingly, the scope of the invention is therefore intended to be limited solely by the scope of the appended claims.

The invention claimed is:

1. A method for producing fuel, the method comprising:
   providing hydrogen produced from a hydrogen production process comprising methane reforming, wherein at least two upgraded biogases are fed to the methane reforming to produce the hydrogen, at least two of the upgraded biogases each being upgraded at a different biogas plant and produced in a process comprising:
   a) collecting biogas comprising methane and carbon dioxide,
   b) capturing carbon dioxide from the collected biogas and producing upgraded biogas, and
   c) providing the captured carbon dioxide for storage;
   feeding the provided hydrogen to a fuel production process that produces the fuel,
   wherein the captured carbon dioxide provided in step (c) of each of the processes is stored and reduces a carbon intensity of the fuel.

2. The method according to claim 1, wherein the fuel production process comprises hydrogenating crude oil derived liquid hydrocarbon with the provided hydrogen to produce the fuel.

3. The method according to claim 1, wherein the fuel production process comprises hydrogenating a renewable feedstock selected from renewable oil and renewable fat with the provided hydrogen to produce the fuel.

4. The method according to claim 1, wherein the fuel comprises gasoline, diesel, jet fuel, or any combination thereof.

5. The method according to claim 1, comprising obtaining one or more fuel credits associated with the hydrogen, the fuel, or a combination thereof.

6. The method according to claim 1, wherein carbon dioxide captured from one of the processes is provided for storage at a separate location than carbon dioxide captured from another of the processes.

7. The method according to claim 1, wherein step (c) of at least one of the processes comprises providing the captured carbon dioxide for geological sequestration.

8. The method according to claim 1, wherein step (c) of at least one of the processes comprises providing the captured carbon dioxide for enhanced oil recovery.

9. The method according to claim 1, wherein step (c) of at least one of the processes comprises providing the captured carbon dioxide for sequestration in concrete.

10. The method according to claim 1, wherein step (c) of at least one of the processes comprises compressing the captured carbon dioxide and injecting the captured carbon dioxide into a carbon dioxide distribution system configured to transport the captured carbon dioxide to storage.

11. The method according to claim 1, wherein step (b) of at least one of the processes comprises capturing the carbon dioxide using carbon dioxide capture selected from cryogenic separation, membrane separation, and absorption with amine solvent.

12. The method according to claim 1, wherein step (b) of at least one of the processes comprises capturing at least 70% of the carbon dioxide originally present in the biogas.

13. The method according to claim 1, wherein the hydrogen is produced using the at least two upgraded biogases and fossil based natural gas.

14. The method according to claim 1, wherein the method does not include storing carbon dioxide produced from the hydrogen production process.

15. The method according to claim 1, wherein at least two of the at least two upgraded biogases are produced from anaerobic digestion, and wherein at least one of the at least two upgraded biogases is derived from organic waste.

16. The method according to claim 1, wherein at least two of the at least two upgraded biogases are produced from anaerobic digestion, and wherein at least one of the at least two upgraded biogases is derived from manure, the manure selected from swine manure and dairy manure.

17. The method according to claim 1, wherein at least two of the at least two upgraded biogases are produced from anaerobic digestion, and wherein at least one of the at least two upgraded biogases is obtained from landfill gas.

18. The method according to claim 1, wherein at least one of the at least two upgraded biogases is transported to a facility at which the hydrogen production process is conducted using a natural gas distribution system.

19. The method according to claim 1, wherein the methane reforming comprises steam methane reforming, and where the at least two upgraded biogases are fed as feedstock to the methane reforming, to a combustion zone of the methane reforming, or a combination thereof.

20. The method according to claim 1, wherein the methane reforming comprises autothermal reforming.

\* \* \* \* \*

UNITED STATES PATENT AND TRADEMARK OFFICE
CERTIFICATE OF CORRECTION

PATENT NO. : 11,946,001 B2
APPLICATION NO. : 18/351862
DATED : April 2, 2024
INVENTOR(S) : Patrick J. Foody It is certified that error appears in the above-identified patent and that said Letters Patent is hereby corrected as shown below:

On the Title Page

On page 4, Column 2 (Other Publications), Line 49, delete "J" and insert -- J. --.

In the Specification

Column 6, Line 34, delete "$O_2$," and insert -- $O_2$, $NH_3$, --.

Column 6, Line 42, delete "$O_2$," and insert -- $O_2$, $NH_3$, --.

Column 9, Line 27, delete "Hz," and insert -- $H_2$, --.

Column 14, Line 24, delete "CHT" and insert -- $CH_4$ --.

Column 14, Line 26, delete "$H_2S$," and insert -- $H_2S$, $O_2$, --.

Column 15, Line 8, delete "e.g.," and insert -- (e.g., --.

Column 17, Line 54, delete "(PDX)," and insert -- (POX), --.

Column 17, Line 58, delete "PDX" and insert -- POX --.

Column 17, Line 59, delete "(TPDX)" and insert -- (TPOX) --.

Column 17, Line 60, delete "(CPDX)," and insert -- (CPOX), --.

Column 17, Line 62, delete "PDX" and insert -- POX --.

Column 17, Line 64, delete "PDX." and insert -- POX. --.

Signed and Sealed this
Seventeenth Day of September, 2024

Katherine Kelly Vidal
*Director of the United States Patent and Trademark Office*

CERTIFICATE OF CORRECTION (continued)
U.S. Pat. No. 11,946,001 B2

Column 18, Line 4, delete "$CH_4 + H_2 + heat \rightarrow CO + 3H_2$" and insert -- $CH_4 + H_2O + heat \rightarrow CO + 3H_2$ --.

Column 18, Line 22, delete "Hz," and insert -- $H_2$, --.

Column 18, Line 23, delete "Hz," and insert -- $H_2$, --.

Column 21, Line 52, delete "captured." and insert -- captured --.

Column 24, Line 36, delete "170ii," and insert -- $170_{ii}$, --.

Column 24, Line 40, delete "170ii," and insert -- $170_{ii}$, --.

Column 24, Line 43, delete "170ii," and insert -- $170_{ii}$, --.